(12) United States Patent
Adam et al.

(10) Patent No.: US 10,299,751 B2
(45) Date of Patent: May 28, 2019

(54) SYSTEMS AND METHODS FOR COLOR VISUALIZATION OF CT IMAGES

(71) Applicant: General Electric Company, Schenectady, NY (US)

(72) Inventors: Vincent Adam, Buc (FR); Saad Sirohey, Pewaukee, WI (US); Guillaume Neveux, Buc (FR); Yannick Le Berre, Buc (FR); Maud Bonnard, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 148 days.

(21) Appl. No.: 15/454,616

(22) Filed: Mar. 9, 2017

(65) Prior Publication Data

US 2017/0265829 A1 Sep. 21, 2017

Related U.S. Application Data

(63) Continuation-in-part of application No. 15/072,071, filed on Mar. 16, 2016.

(51) Int. Cl.
*G06K 9/00* (2006.01)
*A61B 6/00* (2006.01)
*A61B 6/03* (2006.01)

(52) U.S. Cl.
CPC .............. *A61B 6/507* (2013.01); *A61B 6/032* (2013.01); *A61B 6/465* (2013.01); *A61B 6/481* (2013.01); *A61B 6/488* (2013.01); *A61B 6/504* (2013.01); *A61B 6/5264* (2013.01)

(58) Field of Classification Search
None
See application file for complete search history.

(56) References Cited

U.S. PATENT DOCUMENTS

| 5,878,746 A | 3/1999 | Lemelson |
| 7,872,235 B2 | 1/2011 | Rousso et al. |
| 8,364,254 B2 | 1/2013 | Jacquin |
| 2004/0015337 A1 | 1/2004 | Thomas et al. |
| 2004/0121305 A1 | 6/2004 | Wiegand et al. |
| 2005/0215889 A1 | 9/2005 | Patterson |
| 2006/0160074 A1 | 7/2006 | Dorn |
| 2007/0081707 A1 | 4/2007 | Sirohey |
| 2007/0099239 A1 | 5/2007 | Tabibiazar |
| 2007/0198300 A1 | 8/2007 | Duckert et al. |
| 2007/0223796 A1 | 9/2007 | Guehring |
| 2008/0026485 A1 | 1/2008 | Hueber |

*Primary Examiner* — Atiba O Fitzpatrick
(74) *Attorney, Agent, or Firm* — Dean D. Small; The Small Patent Law Group, LLC

(57) ABSTRACT

A computed tomography (CT) imaging system includes a CT imaging unit, a display unit and at least one processor. The CT imaging unit includes an X-ray source and a CT detector. The at least one processor is operably coupled to the imaging unit and the display unit, and is configured to: acquire at least three phases of CT imaging information via the CT imaging unit; determine timing information for imaging intensity of blood vessels represented in the CT imaging information; assign corresponding colors to the blood vessels based on the timing information; reconstruct an image using the CT imaging information from the at least three phases, wherein the blood vessels depicted in the reconstructed image are represented using the corresponding colors based on the timing information; and display the image on the display unit.

23 Claims, 13 Drawing Sheets

SYSTEMS AND METHODS FOR COLOR VISUALIZATION OF CT IMAGES

RELATED APPLICATIONS

The present application is a continuation-in-part of, and claims priority to, U.S. patent application Ser. No. 15/072,071, filed Mar. 16, 2016, entitled "Systems and Methods for Progressive Imaging," the entire subject matter of which is incorporated by reference herein.

BACKGROUND OF THE INVENTION

The subject matter disclosed herein relates generally to systems and methods for imaging, such as computed tomography (CT) imaging, for example to systems and methods for progressive and/or value-based imaging.

Medical imaging may be used to help perform a diagnosis. Certain types of imaging may be completed relatively quickly and/or with relatively low dosage, but provide a relatively lower level of detail, while other types of imaging may be completed more slowly and/or with relatively high dosage, but provide a relatively higher level of detail. In some instances, it may not be known which type of imaging will provide the required level of detail for an accurate diagnosis. Conventionally, in such situations, a physician may order numerous different scans of different levels of detail to be performed, and analyze the results of each scan in attempting to make a diagnosis. However, such performance of a number of scans may result in unnecessary time and/or dosage spent performing scans that were not required for an accurate diagnosis.

BRIEF DESCRIPTION OF THE INVENTION

In one embodiment, a computed tomography (CT) imaging system is provided that includes a CT imaging unit, a display unit and at least one processor. The CT imaging unit includes an X-ray source and a CT detector. The at least one processor is operably coupled to the imaging unit and the display unit, and is configured to: acquire at least three phases of CT imaging information via the CT imaging unit; determine timing information for imaging intensity of blood vessels represented in the CT imaging information; assign corresponding colors to the blood vessels based on the timing information; reconstruct an image using the CT imaging information from the at least three phases, wherein the blood vessels depicted in the reconstructed image are represented using the corresponding colors based on the timing information; and display the image on the display unit.

In another embodiment, a method includes acquiring at least three phases of computed tomography (CT) imaging information via a CT imaging unit that comprises an X-ray source and a CT detector. The method also includes determining, using at least one processor, timing information for imaging intensity of blood vessels represented in the CT imaging information. Further, the method includes assigning corresponding colors to the blood vessels based on the timing information. Also, the method includes reconstructing an image using the CT imaging information from the at least three phases, wherein the blood vessels depicted in the reconstructed image are represented using the corresponding colors based on the timing information. The method further includes displaying the image on a display unit.

In another embodiment, tangible and non-transitory computer readable medium is provided that includes one or more computer software modules. The one or more computer software modules are configured to direct one or more processors to acquire at least three phases of computed tomography (CT) imaging information via a CT imaging unit that comprises an X-ray source and a CT detector; determine timing information for imaging intensity of blood vessels represented in the CT imaging information; assign corresponding colors to the blood vessels based on the timing information; reconstruct an image using the CT imaging information from the at least three phases, wherein the blood vessels depicted in the reconstructed image are represented using the corresponding colors based on the timing information; and display the image on a display unit.

DETAILED DESCRIPTION OF THE INVENTION

Figure 1:
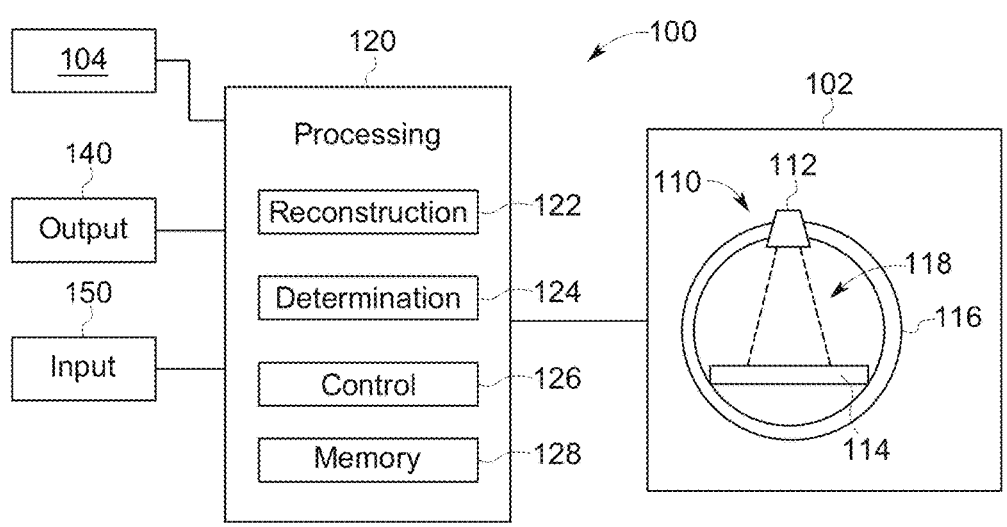
FIG. 1 is a schematic block diagram illustrating an imaging system in accordance with various embodiments.

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for progressive or value-based imaging. Some embodiments related to value based acquisition of medical images for suspected medical conditions of a patient. Various embodiments allow minimal image acquisition through a progressive refinement-based imaging process, while providing evidence (e.g., a displayed image) at each stage to allow a determination to stop further continued acquisition from that patient with a stopping criterion. Imaging information acquisition is continued until a stopping criterion is met. In some embodiments, the stopping criterion is determined using a processor programmed with analysis software coupled to an acquisition system that performs progressive analysis and provides visualization of the analysis results. For example, a human user may choose to stop additional imaging acquisition from the patient based on a displayed image and/or information relating to the displayed image (such as a quantitative measure determined using the displayed image). The progressive refinement-based imaging process may be configured to minimize acquisitional burden while providing progressively more detailed information for improved pathology detection rate. As used herein, acquisitional burden includes at least one of time required, dosage to patient, discomfort to patient, or inconvenience to patient. A varying trade-off between pathology detection rate, speed, and/or patient discomfort may be provided by the imaging process. For example, a first imaging process, for example, may minimize or reduce the time required for a scan, the dosage (radiation and/or contrast) provided to a patient, discomfort to the patient, and/or inconvenience to the patient, while providing a level of certainty for pathology detection. A second scan (and additional scans if appropriate), which may have increased time, dosage, and/or inconvenience, but also have an increased pathology detection rate relative to the first scan, may be performed if the results of the first scan do not provide sufficient certainty regarding a diagnosis.

In one example, imaging of a patient in connection with a stroke analysis is performed. First, non-contrast computed tomography (CT) is acquired. If, based on a non-contrast CT image, it is determined the patient is experiencing hemorrhagic stroke, the imaging process is stopped and surgery is performed to address the hemorrhagic stroke. If the non-contrast CT image does not indicated hemorrhagic stroke, then a subsequent imaging step of acquiring multi-phase CT information is performed, and an image reconstructed using the multi-phase CT information is analyzed to determine if stop criterion (e.g., sufficient collateral filling to permit immediate removal of a clot). If the stop criterion is satisfied, the imaging may be terminated and the patient transferred for surgery. If the stop criterion is not satisfied (e.g., if it is not determinable from the image whether or not there is sufficient collateral filling), the progressive imaging may proceed to acquire CT perfusion imaging data. If the stop criterion is not met following CT perfusion imaging, for example, in some embodiments the progressive imaging may proceed to acquire MR perfusion imaging information.

In another example, an imaging sequence or process may begin with a low dose, thick slice, large coverage CT scan in a first scan for quick assessment of a larger area. A subsequent scan (or scans) may be progressively targeted on a smaller FOV (e.g., an identified lesion and/or particular anatomy) using thinner slices and/or higher dosage.

Generally, in various embodiments, a first type or genre of data of a first modality is acquired, and it is determined if a stop criteria is satisfied after acquiring the first type or genre of data. If the stop criterion is met, no further imaging is performed, but if the stop criterion is not met, a progressively refined second genre of type of data of the first modality (e.g., a more detailed and/or complex type of scan) is performed. As long as stop criteria are not met, the process may be continued by acquiring different genres or types of progressively refined data of the first modality. In some embodiments, after a given number of types of images of a first modality have been reconstructed without satisfying a stop criterion, one or more genres or types of scans of a second imaging modality may be performed. The type of scan and/or modality of scan may be updated until a stop criterion is met or satisfied.

Various embodiments provide improved imaging. A technical effect of at least one embodiment includes reduced number of scans (e.g., by eliminating unnecessary subsequent scans when enough information is available from a previous scan). A technical effect of at least one embodiment includes reduced radiation dose (e.g., by eliminating unnecessary subsequent scans when enough information is available from a previous scan). A technical effect of at least one embodiment includes improved efficiency of performing a series of scans (e.g., by analyzing a previous scan while preparing a subsequent scan). A technical effect of at least one embodiment is to provide images for use in accurate diagnosis of medical conditions such as stroke. A technical effect of at least one embodiment includes reduction of delay between scanning and performing a medical procedure.

FIG. 1 illustrates an imaging system 100 in accordance with an embodiment. The imaging system 100 may be configured, for example, to perform progressive or value-based imaging of a patient using one or more imaging modalities (e.g., computed tomography (CT), X-ray, magnetic resonance imaging (MRI), ultrasound, photon emission tomography (PET), single photon emission computed tomography (SPECT)). The illustrated embodiment, for example, includes a first imaging unit 102 of a first modality, and a second imaging unit 104 of a second modality, as well as a processing unit 120, an output unit (or display) 140, and an input unit 150. For example, the first modality may be CT and the second modality may be MRI. Additional or alternative modality imaging units may be used in various embodiments. Generally, the imaging system 100 is configured to progressively image a patient. The imaging system 100 is configured to acquire a series of image datasets, with each subsequent image dataset requiring more acquisitional burden and/or providing additional diagnostic detail than a preceding image dataset. Before proceeding to perform the next imaging scan in a series, the imaging system 100 (e.g., processing unit 120 either automatically and/or with use of user input) determines if a stop criterion has been reached. If, based on an analysis of an already obtained image, a stop criterion is met, the progressive imaging process is terminated, avoiding more complex imaging scans that take additional time and/or subject the patient to additional dosage (e.g., radiation dosage, contrast dosage). If, however, the stop criterion has not been reached (e.g., the already obtained scans do not provide sufficient information from which to make a diagnostic decision), a subsequent, more detailed, burdensome, and/or complex imaging scan is performed.

As one example, the imaging system may be utilized as part of an analysis of a stroke patient. A first scan may be performed to determine if the patient is experiencing a hemorrhagic stroke or an ischemic stroke. If, based on an image reconstructed using information acquired during the first scan, it is determined that the stroke is hemorrhagic, further scans are not performed, and the patient may be treated for the hemorrhagic stroke. If, however, the stroke is determined to be ischemic, one or more subsequent scans may be performed until an image is obtained from which it is determined whether collateral filling is sufficient to allow for a surgical procedure to remove an identified clot.

Generally, the first imaging unit 102 and the second imaging unit 104 are configured to acquire projection data or imaging data (e.g., CT data or CT imaging information), and the processing unit 120 is configured to reconstruct images using the data acquired by one or more of the imaging units. It may be noted that various embodiments may include additional components, or may not include all of the components shown in FIG. 1 (for example, various embodiments may provide sub-systems for use with other sub-systems to provide an imaging system; various embodiments may only include the first imaging unit 102 of the first modality). Further, it may be noted that certain aspects of the imaging system 100 shown as separate blocks in FIG. 1 may be incorporated into a single physical entity, and/or aspects shown as a single block in FIG. 1 may be shared or divided among two or more physical entities.

The depicted first imaging unit 102 includes a CT acquisition unit 110 which in turn includes an X-ray source 112 and a CT detector 114. (For additional information regarding example CT systems, see FIG. 8 and related discussion herein.) The X-ray source 112 and the CT detector 114 (along with associated components such as bowtie filters, source collimators, detector collimators, or the like (not shown in FIG. 1)) may rotate about a central axis of a bore of a gantry 116 of the system 100.

Generally, X-rays from the X-ray source 112 may be guided to an object to be imaged through a source collimator and bowtie filter. The object to be imaged, for example, may be a human patient or a portion thereof (e.g., head or torso, among others). The source collimator may be configured to allow X-rays within a desired field of view (FOV) to pass through to the object to be imaged while blocking other X-rays. The bowtie filter module may be configured to absorb radiation from the X-ray source 112 to control distribution of X-rays passed to the object to be imaged.

X-rays that pass through the object to be imaged are attenuated by the object and received by the CT detector 114 (which may have a detector collimator associated therewith), which detects the attenuated X-rays and provides imaging information to the processing unit 120. The processing unit 120 may then reconstruct an image of the scanned portion of the object using the imaging information (or projection information) provided by the CT detector 114. The processing unit 120 includes or is operably coupled to the output unit 140, which in the illustrated embodiment is configured to display an image, for example, an image reconstructed by the processing unit 120 using imaging information from the CT detector 114. The depicted input unit 150 is configured to obtain input corresponding to a scan to be performed, with the processing unit 120 using the input to determine one or more scan settings (e.g., tube voltage, tube current, scanning rotation speed, or the like). The input unit 150 may include a keyboard, mouse, touchscreen or the like to receive input from an operator, and/or may include a port or other connectivity device to receive input from a computer or other source.

In the illustrated embodiment, the X-ray source 112 is configured to rotate about the object. For example, the X-ray source 112 and the CT detector 114 may be positioned about a bore 118 of the gantry 116 and rotated about the object to be imaged. As the X-ray source 112 rotates about the object during an imaging scan, X-rays received by the CT detector 114 during one complete rotation provide a 360 degree view of X-rays that have passed through the object. Other imaging scanning ranges may be used in alternative embodiments. The CT imaging information may be collected as a series of views that together make up a rotation or portion thereof. A blanking interval for may separate a first view or projection from the next view or projection in the series.

As indicated herein, the processing unit 120 is configured to control various aspects of the acquisition units and/or to reconstruct an image using information obtained via the acquisition units. For example, the processing unit 120 may be configured to reconstruct a CT image (or a series of CT images using information acquired at different times) using information collected by the CT acquisition unit 110.

The depicted processing unit 120 is operably coupled to the input unit 150, the output unit 140, the first imaging unit 102, and the second imaging unit 104. The processing unit 120, for example, may receive information regarding a scan from the input unit 150 that may be utilized in determining scanning parameters to be used in acquiring CT imaging information. The processing unit 120 in various embodiments receive user inputs from the input unit 150 that correspond to satisfaction (or lack thereof) of a stop criterion (e.g., whether information is sufficient from an already performed scan to make performance of a subsequent scan or scans necessary or desirable). As another example, the processing unit 120 may receive imaging data or projection data from the imaging units (e.g., CT detector 114). As one more example, the processing unit 120 may provide control signals to one or more aspects of the imaging units, such as the CT acquisition unit 110, for example the X-ray source 112 and CT detector 114. The processing unit 120 may include processing circuitry configured to perform one or more tasks, functions, or steps discussed herein. It may be noted that "processing unit" as used herein is not intended to necessarily be limited to a single processor or computer. For example, the processing unit 120 may include multiple processors and/or computers, which may be integrated in a common housing or unit, or which may distributed among various units or housings.

The depicted processing unit 120 is configured to control the first imaging unit 102 and the second imaging unit 104 to acquire imaging information. For example, the depicted processing unit 12 is configured to control the CT acquisition unit 110 (e.g., by controlling the activation and deactivation of the X-ray source 112) to collect CT imaging information during an imaging scan. The processing unit 120 in the illustrated embodiment is configured to control the CT acquisition unit 110 to acquire different types of imaging information using different scan procedures. For example, the depicted processing unit 120 is configured to control the CT acquisition unit 110 to perform non-contrast CT imaging scans, multi-phase CT imaging scans, and CT perfusion imaging scans.

In the embodiment depicted in FIG. 1, the processing unit includes a reconstruction module 122, a determination module 124, a control module 126, and a memory 128. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein (e.g., method 200 or aspects thereof).

The depicted reconstruction module 122 is configured to reconstruct one or more images using imaging or projection data acquired from the first imaging unit 102 and/or the second imaging unit 104 (e.g., from the CT detector 114 of the first imaging unit 102). For example, the reconstruction module 122 may receive imaging information from the CT detector 114 taken over a number of views (e.g., for a full rotation or portion thereof, or for a number of rotations taken at different positions along the length of an object to be imaged) and reconstruct an image used for diagnostic purposes.

In the illustrated embodiment, the determination module 124 is configured to receive information from the first imaging unit 102 and/or the second imaging unit 104 (e.g., CT imaging information from the CT acquisition unit 110), and/or information from the reconstruction module 122 (e.g., a reconstructed image) and/or the input unit 150 (e.g., information corresponding to a stop criterion, such as a user input indicating satisfaction or dissatisfaction of a stop criterion), and to determine, for example, whether a stop criterion has been satisfied or whether a subsequent scan should be performed. In some embodiments, the determination module 124 determines the type of subsequent scan to be performed.

For example, the determination module 124 may first determine if a stop criterion has been satisfied. In some embodiments, the determination module 124 determines if a stop criterion is satisfied based on an objective or measurable parameter (or parameters) automatically determined via analysis of a reconstructed image. In some embodiments, the determination module 124 determines if a stop criterion is satisfied based on receipt (or failure to receive) a user input. For instance, in some embodiments, the determination module 124 (or other aspect of processing unit 120) determines that a given stop criterion is not satisfied if an input corresponding to a satisfaction of the given stop criterion is not received within a predetermined amount of time after displaying a corresponding image. For example, after display of a given reconstructed image, the determination module 124 may begin a timing period. If no input is received from an operator before expiration of the timing period, the determination module 124 determines that the stop criterion has not been satisfied, and the processing unit 120 controls the imaging system 100 to acquire the next, more detailed or complex imaging scan in a series.

In one example scenario, a patient experiencing a stroke may be diagnosed using a progressive imaging process using the imaging system 100. In the example scenario, a sequence of up to three CT imaging scans are performed, with each subsequent scan having additional acquisitional burden relative to the preceding scan, as necessary. The first imaging scan is a non-contrast CT imaging scan, the second imaging scan is a multi-phase CT imaging scan, and the third imaging scan is a perfusion CT imaging scan. A different stop criterion is employed for the first and second scans.

In the example scenario, after the CT imaging information has been collected with the CT acquisition unit 110, the reconstruction module 122 reconstructs a non-contrast image, and the image (which may have undergone postprocessing to assist in diagnosis) is displayed via the output unit 140. The stop criterion for the first scan in the example scenario corresponds to a determination of a level of bleeding corresponding to hemorrhagic stroke. The satisfaction of the stop criterion in the example scenario is based on a user input. If a user provides an input to the input unit 150 indicating that an amount of bleeding corresponding to hemorrhagic stroke has been determined based on the displayed image, the determination module 124 determines that a stop criterion has been met and no further scans are performed. Instead, the patient may be treated for hemorrhagic stroke without further delay for additional scans. If, however, the user provides an input indicating that an amount of bleeding corresponding to hemorrhagic stroke has not been identified (or fails to provide an input within a predetermined time period), the determination module 124 determines that a stop criterion has not been satisfied, and a subsequent scan is performed.

In the example scenario, the subsequent scan is a multi-phase CT angiography (CTA) exam. A contrast agent is introduced to the patient, and the CT acquisition unit 110 acquires multi-phase CTA imaging information. Multi-phase CTA provides temporal information regarding blood vessels, for example that may be used to help determine an extent of arterial filling in the brain for ischemic stroke patients. If sufficient arterial filling is determined, a clot may be identified and removed; however, if filling is insufficient, there may be a risk of blood vessel rupture due to pressure change after removal of a clot. After the CT imaging information has been collected with the CT acquisition unit 110, the reconstruction module 122 reconstructs an image or images (e.g., one or more images corresponding to vessels of the brain at different phases or points in time), and the image (which may have undergone postprocessing to assist in diagnosis) is displayed via the output unit 140. The stop criterion for the second scan in the example scenario corresponds to a determination of a sufficient level of collateral filling of blood vessels (e.g., a sufficient level to permit removal of a clot without undue risk of vessel rupture). The satisfaction of the second stop criterion in the example scenario is based on a user input. If a user provides an input to the input unit 150 indicating that a sufficient level of collateral filling has been determined based on the displayed image, the determination module 124 determines that a stop criterion has been met and no further scans are performed. Instead, the patient may be treated for ischemic stroke (e.g., removal of a clot) without further delay for additional scans. If, however, the user provides an input indicating an insufficient level of collateral filling or an inability to determine whether or not a sufficient level of collateral filling exists (or the user fails to provide an input within a predetermined time period), the determination module 124 determines that a stop criterion has not been satisfied, and a subsequent scan is performed.

In the example scenario, the subsequent scan is a CT perfusion exam. After the contrast agent associated with the multi-phase CTA exam has sufficiently washed out, a different contrast agent is introduced to the patient for CT perfusion analysis, and the CT acquisition unit 110 acquires CT perfusion imaging information. Multi-phase CTA provides information regarding brain tissue and whether sufficient blood flow is being provided to keep tissue alive. If multi-phase CTA imaging information was not sufficient to determine whether or not collateral filling was sufficient, CT perfusion information may be acquired to better determine whether or not collateral filling was sufficient.

It may be noted that the various imaging scans in a progressive series of scans may have corresponding scanning parameters or settings (e.g., parameters or settings used to acquire information) as well as display parameters or settings (e.g., parameters or settings used in postprocessing for convenient display). In some embodiments, the determination module 124 (and/or other aspect or portion of the processing unit 120) determines a subsequent type of scan to be performed, as well as scanning and display parameters. For example, in some embodiments, for a progressive stroke imaging sequence, if a stop criterion is not satisfied after analysis of a non-contrast CT image, the determination module 124 determines that a multi-phase CTA imaging scan is to be performed, and directs to the control module 124 to use appropriate settings for multi-phase CTA image acquisition. Further, the determination module 124 determines that a postprocessing routine tailored for use with multi-phase CTA is to be used, and provides the appropriate information to the reconstruction module 122 (or other aspect of the processing unit 120) for use in postprocessing and displaying an image reconstructed using the multi-phase CTA imaging information.

In the illustrated embodiment, the determination module 124 is communicably coupled to the control module 126, with the control module 126 configured to control the first imaging unit 102 and/or the second imaging unit 104 (e.g., the CT acquisition unit 110 and/or other aspects of the system 100), and to perform the imaging scans called for by the determination module 124.

The output unit 140 is configured to provide information to the user. The output unit 140 is configured to display, for example, an image (e.g., an image that has been reconstructed and postprocessed as discussed herein). Additionally, the output unit 140 may provide, among other things, guidance regarding determination of a stop criterion, display a timer indicating when the determination module 124 will determine failure to satisfy satisfaction of stop criterion absent a contrary input, measured or determined parameters corresponding to a displayed image. The output unit 140 may include one or more of a screen, a touchscreen, a printer, or the like.

The input unit 150 may be configured to obtain an input that corresponds to one or more settings or characteristics of a scan or progressive series of scans to be performed, and to provide the input (or information corresponding to the input) to the processing unit 120, which may use the input to determine, adjust, or select settings used to acquire imaging information, reconstruct imaging information, postprocess or otherwise prepare one or more images for display, or the like. For example, the input unit 150 may receive an instruction specifying a procedure, and the processing unit then determines the appropriate sequence of scans and corresponding reconstruction and postprocessing routines. The input may include, for example, a type of progressive imaging to perform, such as stroke analysis. Responsive to receiving the input from the input unit 150, the processing unit 120 automatically initiates a corresponding series of scans, which may be selectively performed until a stop criterion is satisfied. The input unit 150 may be configured to accept a manual user input, such as via a touchscreen, keyboard, mouse, or the like. Additionally or alternatively, the input unit 150 may receive information from another aspect of the imaging system 100, another system, or a remote computer, for example, via a port or other connectivity device. In various embodiments, the input unit 150 also receives input regarding criteria satisfaction. In some embodiments, a user may provide input, based on visual inspection of a displayed image, whether or not a stop criterion is satisfied (and/or whether the image does not provide enough information to make a determination). In some embodiments, a user may provide an indication if a stop criterion is satisfied, and the processing unit 120 may automatically proceed to a next scan in a series if no input is received within a predetermined time period. Use of a predetermined time period for automatically advancing to a subsequent imaging stage reduces the amount of time taken for a series of scans in various embodiments.

Figure 2:
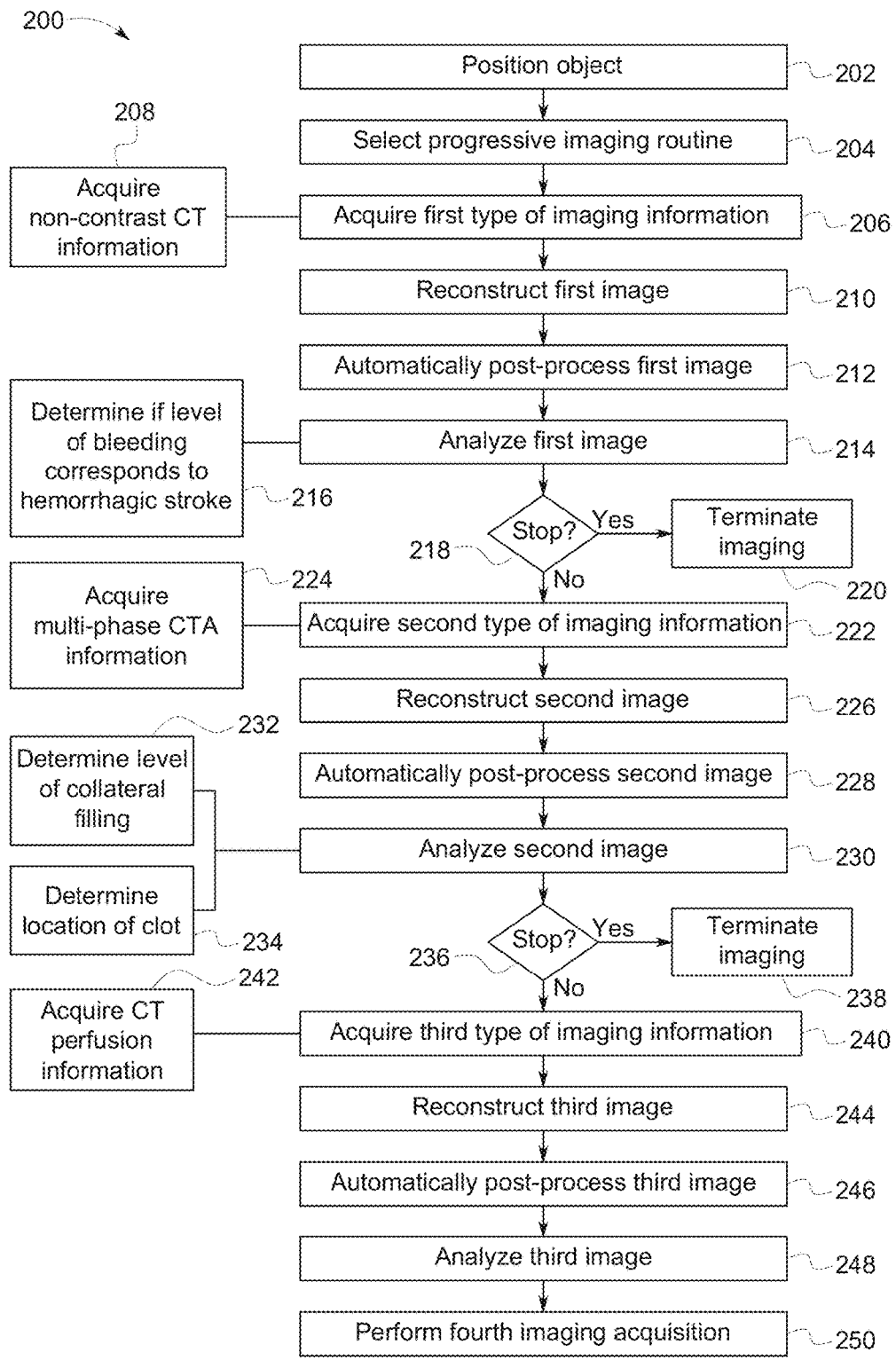
FIG. 2 is a flowchart of a method in accordance with various embodiments.

FIG. 2 provides a flowchart of a method 200 for progressively imaging an object, for example a patient as part of a stroke analysis, in accordance with various embodiments. The method 200, for example, may employ or be performed by structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be able to be used as one or more algorithms to direct hardware (e.g., one or more aspects of the processing unit 120) to perform one or more operations described herein.

At 202, the object (e.g., patient is positioned). For example, the object may be a human patient positioned on a table in a bore of an imaging system (e.g., first imaging unit 102 or second imaging unit 104), which may include, for example, a CT acquisition unit (e.g., CT acquisition unit 110).

Figure 3:
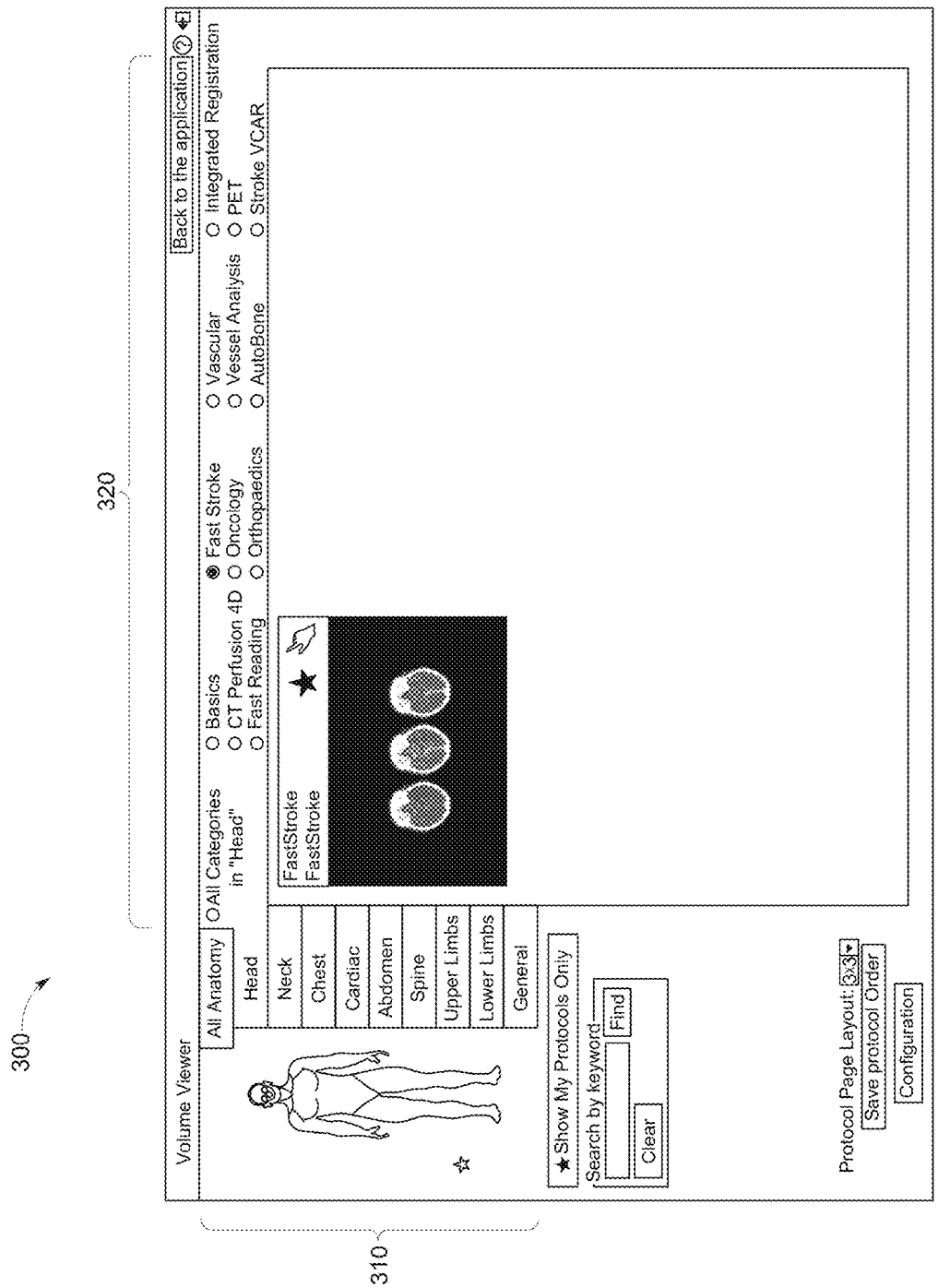
FIG. 3 illustrates an example display in accordance with various embodiments.

At 204, a progressive imaging routine or procedure is selected. The progressive imaging routine in various embodiments specifies a series of scans of increasing acquisitional burden or detail that are performed to aid in diagnosis of a condition. For example, for a stroke diagnosis progressive imaging routine, a series of scans may include a non-contrast CT scan, a multi-phase contrast CTA scan, and a CT perfusion scan. The progressive imaging routine may be selected or determined based on a user input provided to processing unit (e.g., to processing unit 120 via input unit 150). FIG. 3 provides an example illustration of a display 300 in accordance with various embodiments which a user may use to provide an input to select a progressive imaging routine. The display 300 includes various user guidance features 310, which allow a user to specify a portion of the body to be scanned. As seen in FIG. 3, the depicted display also includes user selection buttons 320 corresponding to available scanning procedures. In the illustrated embodiment, the user has selected "Fast Stroke." Responsive to the user selection, a processing unit may prepare a system to perform the series of scans using predetermined acquisition, reconstruction, and display parameters for the selected routine.

At 206, a first type of imaging information is acquired. For example, the first type of imaging information in various embodiments is acquired using a first modality of a first imaging unit. In some embodiments, the first type of imaging information is non-contrast information. In some embodiments, an X-ray source and detector may be rotated about the object being imaged and operated in a manner prescribed by predetermined scanning parameters to collect imaging information at a detector. As one example, in the illustrated embodiment, at 208, the first type of diagnostic imaging information is non-contrast CT (e.g., acquired via CT acquisition unit 110), and the first stop criterion is a determination of a level of bleeding corresponding to hemorrhagic stroke.

Figure 4:
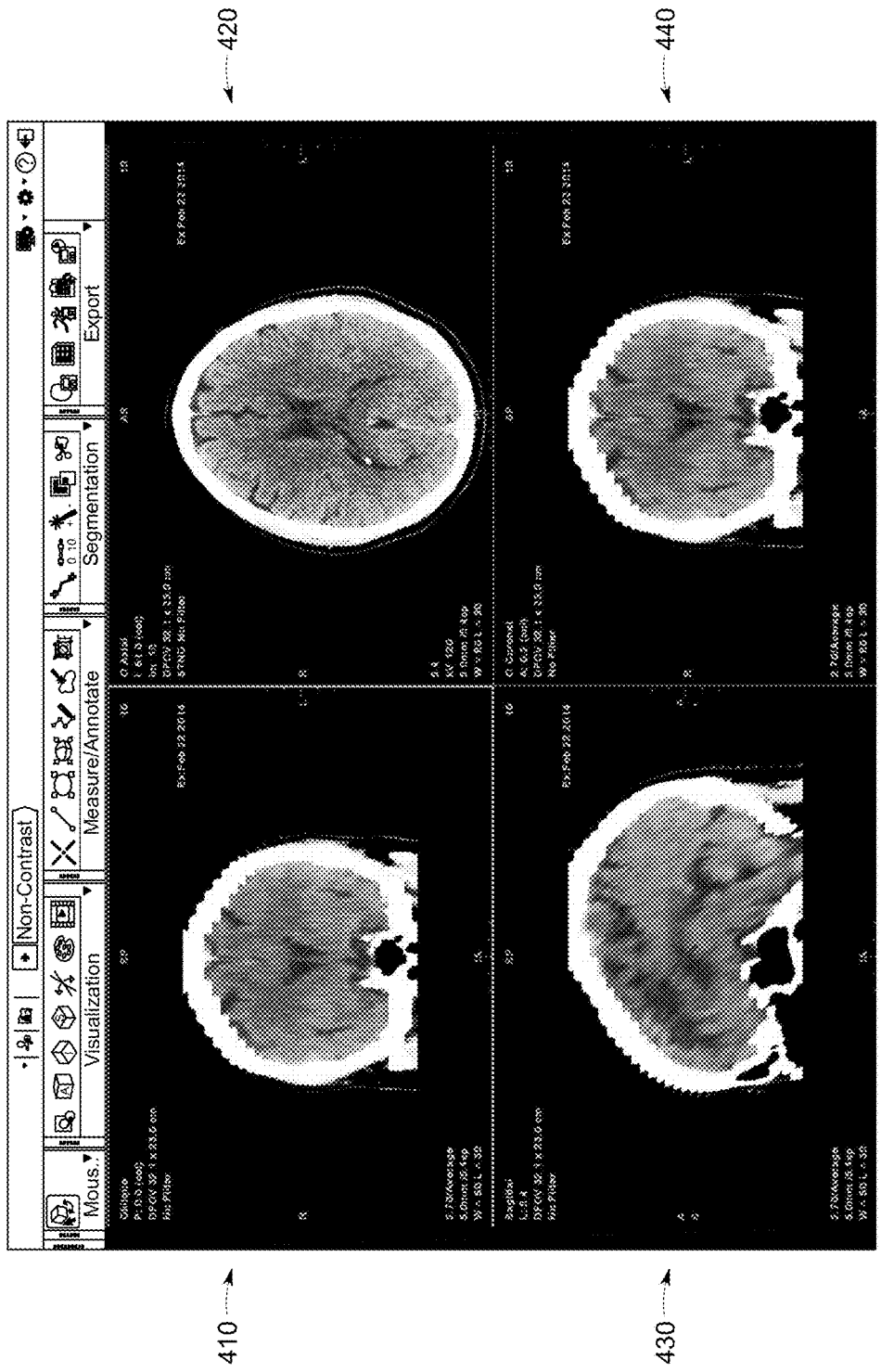
FIG. 4 illustrates an example display in accordance with various embodiments.

At 210, a first image is reconstructed. The first image is reconstructed using the first imaging information acquired at 206. At 212, the reconstructed image is automatically postprocessed. For example, in various embodiments, a processing unit (e.g., processing unit 120) may postprocess the reconstructed first image using a predetermined postprocessing routine based on the selected progressive imaging routine to provide a user with a convenient, easily usable display for determining if a stop criterion is satisfied. FIG. 4 illustrates an example non-contrast CT display 400 in accordance with various embodiments. The display 400 includes four views (namely, an oblique view 410, an axial view 420, a sagittal view 430, and a coronal view 440) which may be used by a viewer of the display to determine if there is a level of bleeding corresponding to hemorrhagic stroke present or not.

At 214, the first image is analyzed to determine if a first stop criterion for terminating imaging is satisfied by the first image. The analysis in some embodiments may be performed by an operator or user viewing an image on a display (e.g., display unit 140). It may be noted that the display may be remote from other aspects of an imaging system, so that a physician not present at a scanning facility may determine if a stop criterion has been satisfied. In some embodiments, a processing unit (e.g., processing unit 120) may be configured to analyze one or more determinable parameters or objective measurements corresponding to a reconstructed image to determine if a stop criterion has been met. In the depicted embodiment, at 216, the first image is analyzed to determine if a level of bleeding corresponding to hemorrhagic stroke is present.

At 218, it is determined if the first stop criterion has been met or satisfied. Generally, if a stop criterion is met, the progressive imaging routine may be terminated before performing additional, more complex scans that are unnecessary if an earlier scan provides sufficient information for a particular diagnosis. If the first stop criterion is met, the method 200 proceeds to 220 and the imaging series is terminated. If the stop criterion is not met or satisfied, the method proceeds to 222. For example, if a level of bleeding consistent with hemorrhagic stroke is present, the patient may be transferred from the imaging device for treatment of the hemorrhagic stroke immediately, without spending additional time performing scans. If, however, the level of bleeding does not correspond to hemorrhagic stroke, an ischemic stroke may be diagnosed, for which additional imaging will be beneficial, for example, to determine a location of a clot as well as the extent of collateral filling.

At 222, a second type of diagnostic imaging information is acquired. For example, in various embodiments, the second type of diagnostic imaging information is of the same, first modality as the first type of diagnostic imaging information, is acquired with the same, first imaging unit, and has an increased level of acquisitional burden relative to the first type of diagnostic imaging information. In some embodiments, the second type of imaging information is multi-phase CTA information. For example, in the illustrated embodiment, at 224, the second type of diagnostic imaging information is multi-phase CTA information, and the second stop criterion is determination of a sufficient level of collateral filling of blood vessels. In the illustrated embodiment, a contrast agent is introduced in the patient before acquiring CT information as part of a multi-phase CTA imaging process.

Figure 5:
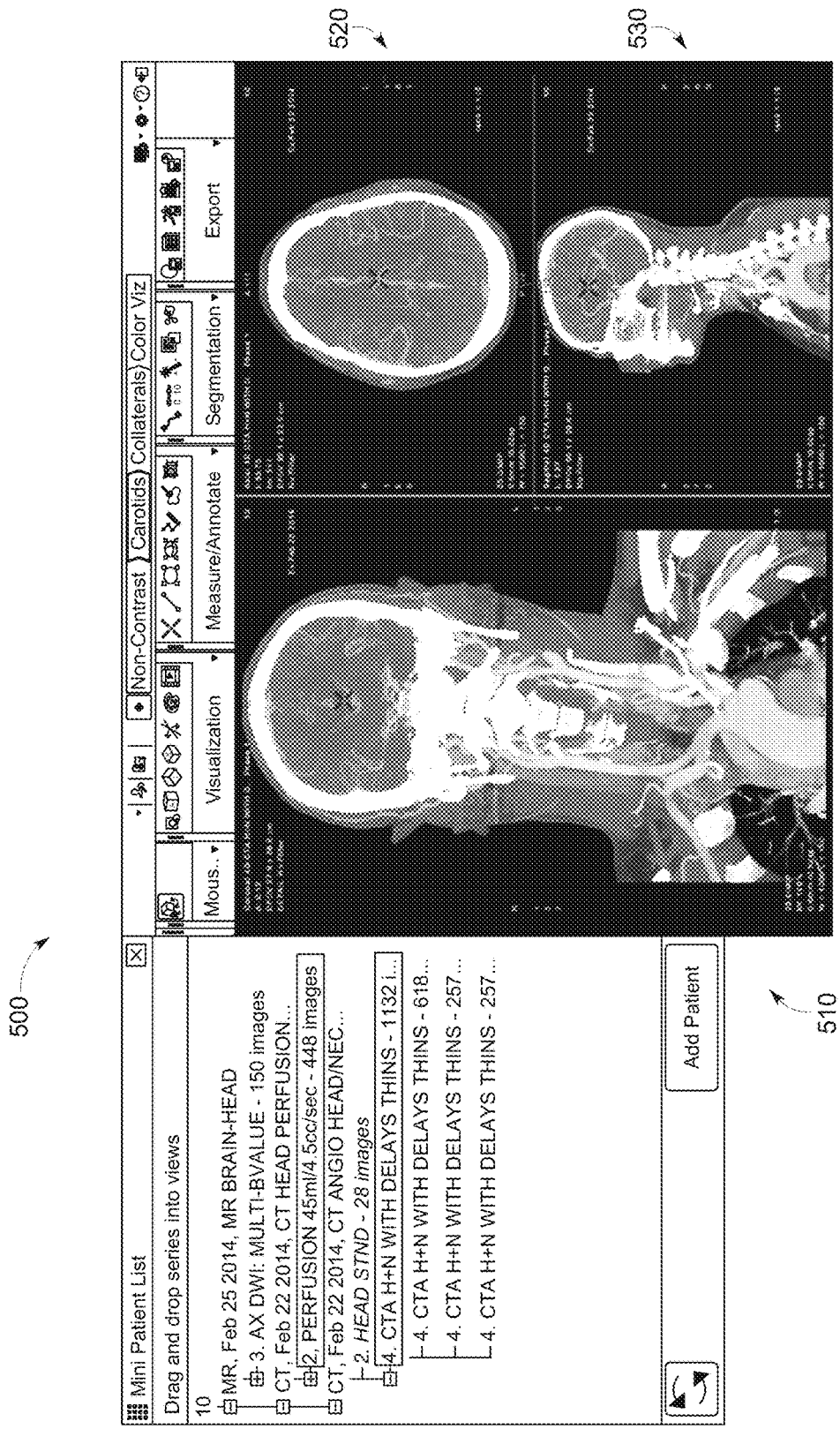
FIG. 5 illustrates an example display in accordance with various embodiments.
Figure 6:
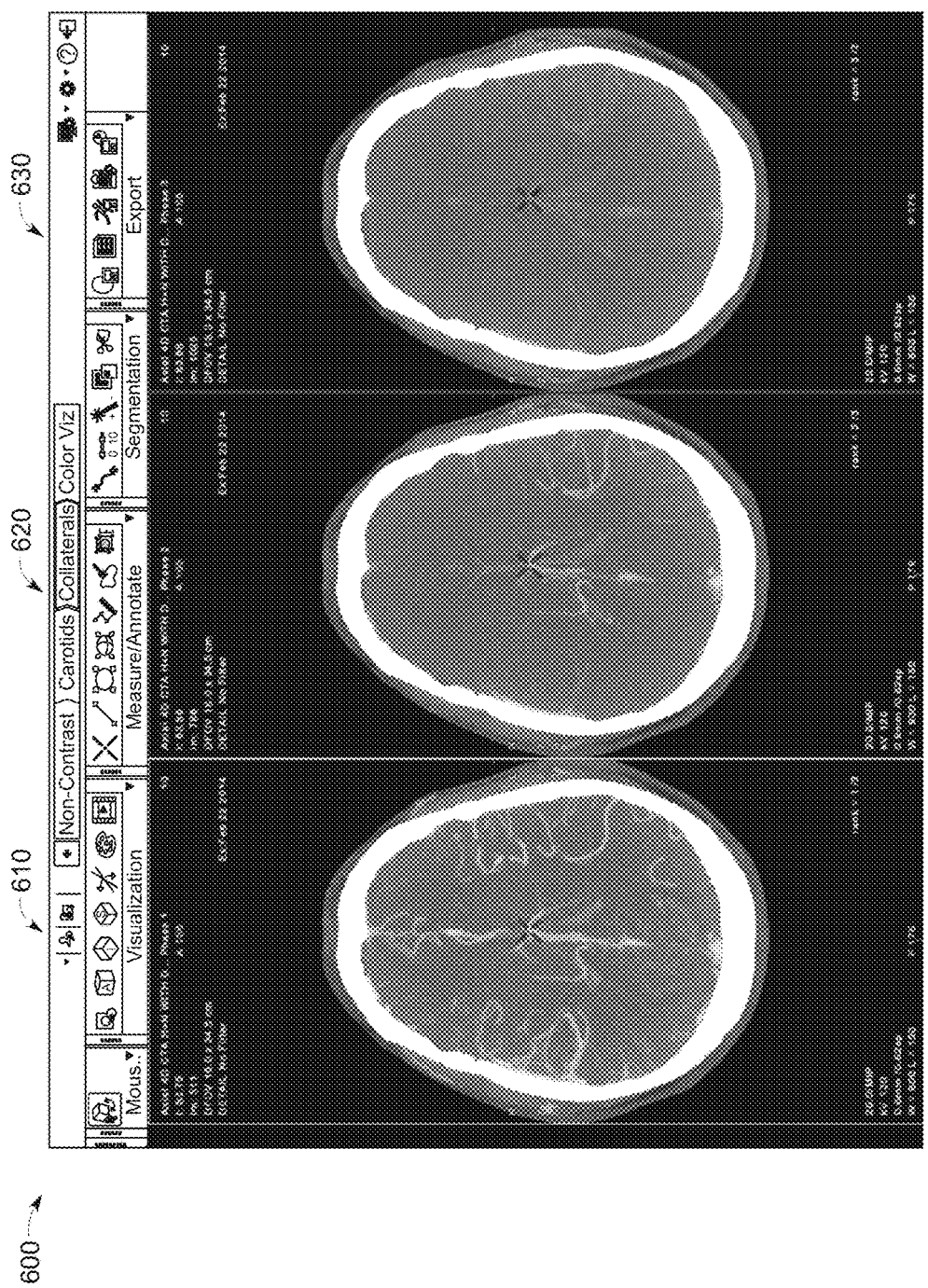
FIG. 6 illustrates an example display in accordance with various embodiments.

At 226, a second image is reconstructed. The first image is reconstructed using the second type of diagnostic imaging information acquired at 222. At 228, the reconstructed image is automatically postprocessed. For example, in various embodiments, a processing unit (e.g., processing unit 120) may postprocess the reconstructed second image using a predetermined postprocessing routine (e.g., postprocessing tailored for multi-phase CTA) based on the selected progressive imaging routine to provide a user with a convenient, easily usable display for determining if a stop criterion is satisfied. FIG. 5 illustrates an example CTA display 500, and FIG. 6 illustrates an example CTA display 600 in accordance with various embodiments. The processing unit 120, responsive to receiving the image reconstructed at 226, in various embodiments automatically performs postprocessing on the image reconstructed at 226 to prepare the display 500 and display 600 for use. The display 500 displays carotids as part of a maximum intensity projection (MIP) in three different views—a coronal view 510, an axial view 520, and a sagittal view 530. The display 600 displays three axial views at different times or phases—a first phase view 610, a second phase view 620, and third phase view 630. The display 500 and display 600 may be used by a viewer to determine if there is sufficient collateral filling. For example, if there is sufficient collateral filling, the patient may proceed to an endovascular procedure to remove a clot, but if not, an alternative course may be selected due to the risk of rupturing blood vessels due to a pressure change after clot removal.

At 230, the second image is analyzed to determine if a second stop criterion for terminating imaging is satisfied by the second image. The analysis in some embodiments may be performed by an operator or user viewing an image or images on a display (e.g., display unit 140). It may be noted that the display may be remote from other aspects of an imaging system, so that a physician not present at a scanning facility may determine if a stop criterion has been satisfied. In some embodiments, a processing unit (e.g., processing unit 120) may be configured to analyze one or more determinable parameters or objective measurements corresponding to a reconstructed image to determine if a stop criterion has been met. In the depicted embodiment, at 232, the first image is analyzed by a viewer of a display to determine if there is sufficient collateral filling to permit clot removal. It may be noted that a location of a clot to be removed may also be determined at 234 in various embodiments.

At 236, it is determined if the second stop criterion has been met or satisfied. If the second stop criterion is met, the method 200 proceeds to 238 and the imaging series is terminated. If the stop criterion is not met or satisfied, the method proceeds to 240. For example, if sufficient collateral filling is present, the patient may be transferred from the imaging device for treatment of the ischemic stroke (e.g., removal of an identified clot) immediately, without spending additional time performing scans. If, however, the level of collateral filling is not sufficient, or if it cannot be determined from the multi-phase CTA analysis if collateral filling is sufficient, additional imaging may be beneficial, for example, to determine the extent of collateral filling.

At 240, a third type of diagnostic imaging information is acquired. For example, in various embodiments, the third type of diagnostic imaging information is of the same, first modality as the first type and second type of diagnostic imaging information, is acquired with the same, first imaging unit, and has an increased level of acquisitional burden relative to the second type of diagnostic imaging information. In the illustrated embodiment, at 242, the third type of diagnostic imaging information is CT perfusion information. CTA may be understood as looking at vessels at a macro-level, and CT perfusion may provide additional complexity or detail by providing information regarding the patient at a tissue level. Tissue level parameters are calculated as part of a CT perfusion analysis in various embodiments to provide one or more quantitative measures to assist in determining a level of collateral filling. In the illustrated embodiment, a contrast agent is introduced in the patient before acquiring CT information as part of a CT perfusion imaging process. In various embodiments, the reconstruction and associated analysis regarding the second imaging information may be performed during a washout period of contrast agent used in acquiring the second imaging information. It may also be noted that, in various embodiments, the patient is maintained on a table of the first imaging unit during the acquiring of the second type of diagnostic imaging information, reconstructing of the second image, analyzing of the second image, and acquiring of the third type of diagnostic imaging information.

Figure 7:
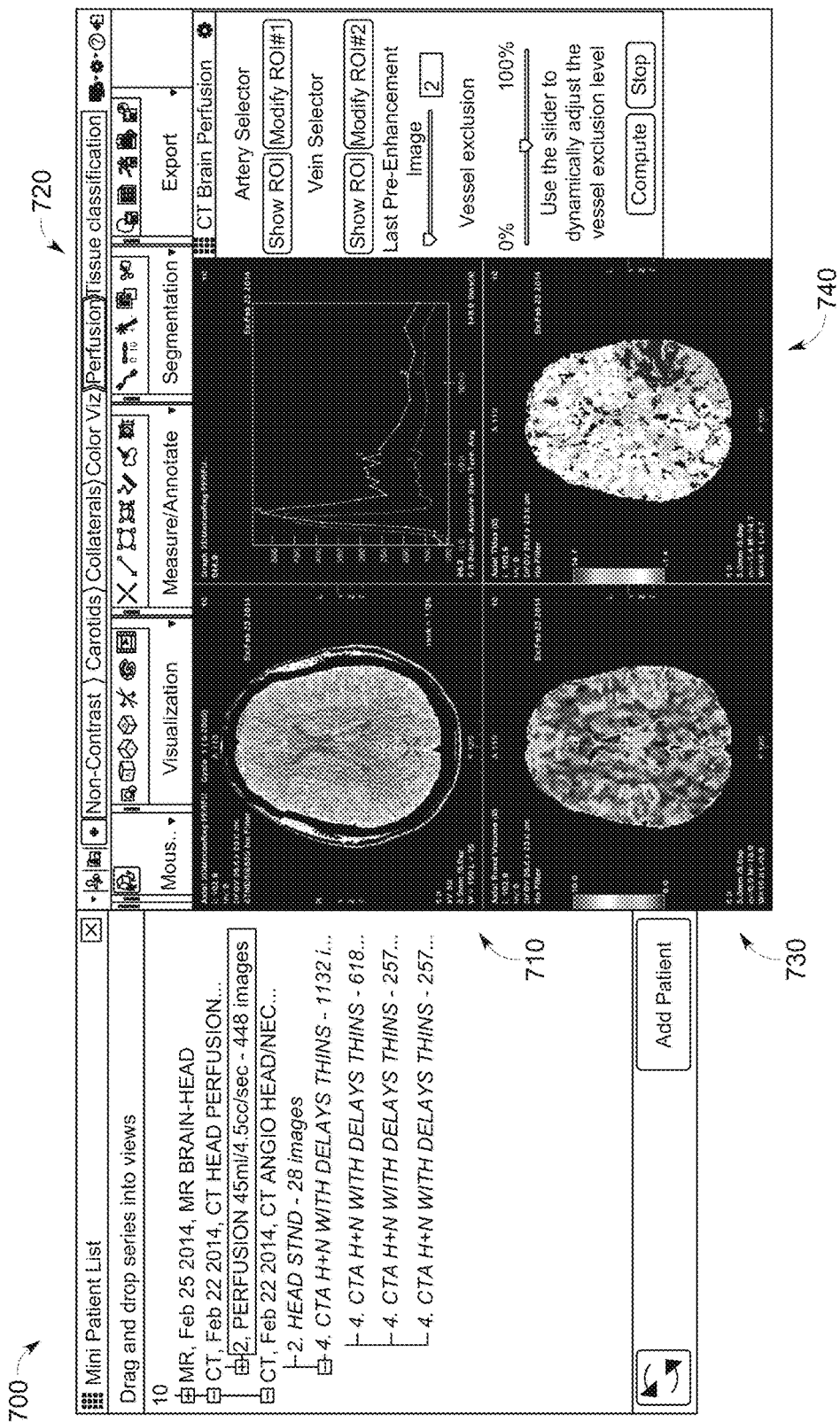
FIG. 7 illustrates an example display in accordance with various embodiments.

At 244, a third image is reconstructed. The third image is reconstructed using the third type of diagnostic imaging information acquired at 240. At 246, the reconstructed image is automatically postprocessed. For example, in various embodiments, a processing unit (e.g., processing unit 120) may postprocess the reconstructed third image using a predetermined postprocessing routine (e.g., postprocessing tailored for CT perfusion) based on the selected progressive imaging routine to provide a user with a convenient, easily usable display. FIG. 7 illustrates an example CT perfusion 700 in accordance with various embodiments. The processing unit 120, responsive to receiving the image reconstructed at 244, in various embodiments automatically performs postprocessing on the image reconstructed at 244 to prepare the display 700 for use. The display 700 includes image views, 710, 730, and 740, as well as graph 720 corresponding to one or more quantitative measures. The particular views presented and format of the presented views for the display 700 (and/or other displays discussed herein) in various embodiments is automatically selected by a processing unit, for example, based on predetermined viewer preferences. For example, responsive to receiving a given type of reconstructed image, the processing unit may automatically selected a predetermined postprocessing routine corresponding to the given type of reconstructed image to prepare a display for viewing.

At 248, the third image is analyzed (e.g., to determine if a stop criterion is met if any additional scans remain in the progressive imaging routine). The analysis in some embodiments may be performed by an operator or user viewing an image or images on a display (e.g., display unit 140). It may be noted that the display may be remote from other aspects of an imaging system, so that a physician not present at a scanning facility may determine if a stop criterion has been satisfied. In some embodiments, a processing unit (e.g., processing unit 120) may be configured to analyze one or more determinable parameters or objective measurements (e.g., one or more quantitative measures provided by a CT perfusion imaging process) corresponding to a reconstructed image to determine if a stop criterion has been met. In some embodiments, the third image is analyzed for collateral filling, and a corresponding stop criterion is if a sufficient amount of collateral filling is determined to allow the patient to be transferred to have surgery to remove a clot.

At 250, in the illustrated embodiment, a fourth imaging acquisition is performed. The fourth imaging acquisition in various embodiments uses a different, second modality than was used for the first, second, and third types of diagnostic information. For example, CT may be employed for the first, second, and third types of diagnostic information, but the fourth imaging acquisition may be performed using MRI. In some embodiments, the fourth imaging acquisition, may be performed to provide additional complexity or detail to information previously acquired, while in other embodiments the fourth imaging acquisition may be used to provide information for a different anatomical structure or diagnosis. In various embodiments, the fourth imaging acquisition is performed only if a stop criterion corresponding to the third type of diagnostic imaging information is not satisfied.

It may be noted that a number of imaging stages or acquisitions (or potential imaging stages or acquisition) may vary in different embodiments. Generally, in some embodiments, each imaging stage or step includes an acquisition, a reconstruction, a display, an analysis, and a determination if a stop criterion has been met. The sequence may be repeated for each subsequent stage or step (e.g., using different imaging techniques) until a stop criterion is met.

Figure 8:
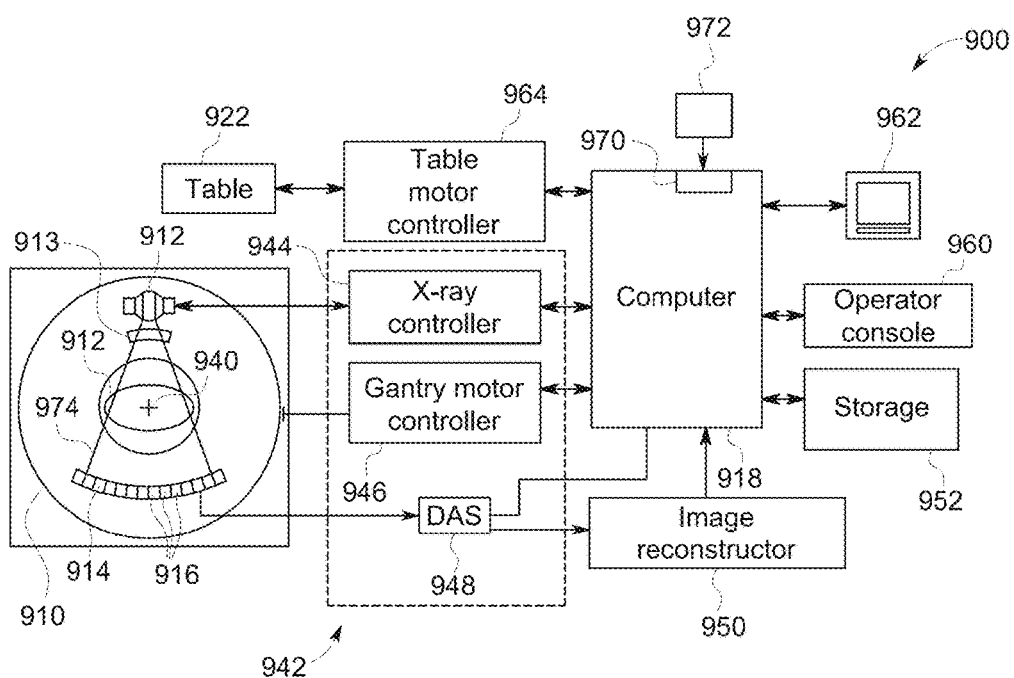
FIG. 8 is a schematic block diagram of an imaging system in accordance with various embodiments.

Various methods and/or systems (and/or aspects thereof) described herein may be implemented using a medical imaging system. For example, FIG. 8 is a block schematic diagram of an exemplary CT imaging system 900 that may be utilized to implement various embodiments discussed herein. Although the CT imaging system 900 is illustrated as a standalone imaging system, it should be noted that the CT imaging system 900 may form part of a multi-modality imaging system in some embodiments. For example, the multi-modality imaging system may include the CT imaging system 900 and a positron emission tomography (PET) imaging system, or a single photon emission computed tomography (SPECT) imaging system. It should also be understood that other imaging systems capable of performing the functions described herein are contemplated as being used.

The CT imaging system 900 includes a gantry 910 that has the X-ray source 912 that projects a beam of X-rays toward the detector array 914 on the opposite side of the gantry 910. A source collimator 913 is provided proximate the X-ray source 912. In various embodiments, the source collimator 913 may be configured to provide wide collimation as discussed herein. The detector array 914 includes a plurality of detector elements 916 that are arranged in rows and channels that together sense the projected X-rays that pass through a subject 917. The imaging system 900 also includes a computer 918 that receives the projection data from the detector array 914 and processes the projection data to reconstruct an image of the subject 917. The computer 918, for example, may include one or more aspects of the processing unit 120, or be operably coupled to one or more aspects of the processing unit 120. In operation, operator supplied commands and parameters are used by the computer 918 to provide control signals and information to reposition a motorized table 922. More specifically, the motorized table 922 is utilized to move the subject 917 into and out of the gantry 910. Particularly, the table 922 moves at least a portion of the subject 917 through a gantry opening (not shown) that extends through the gantry 910. Further, the table 922 may be used to move the subject 917 vertically within the bore of the gantry 910.

The depicted detector array 914 includes a plurality of detector elements 916. Each detector element 916 produces an electrical signal, or output, that represents the intensity of an impinging X-ray beam and hence allows estimation of the attenuation of the beam as it passes through the subject 917. During a scan to acquire the X-ray projection data, the gantry 910 and the components mounted thereon rotate about a center of rotation 940. FIG. 8 shows only a single row of detector elements 916 (i.e., a detector row). However, the multislice detector array 914 includes a plurality of parallel detector rows of detector elements 916 such that projection data corresponding to a plurality of slices can be acquired simultaneously during a scan.

Rotation of the gantry 910 and the operation of the X-ray source 912 are governed by a control mechanism 942. The control mechanism 942 includes an X-ray controller 944 that provides power and timing signals to the X-ray source 912 and a gantry motor controller 946 that controls the rotational speed and position of the gantry 910. A data acquisition system (DAS) 948 in the control mechanism 942 samples analog data from detector elements 916 and converts the data to digital signals for subsequent processing. An image reconstructor 950 receives the sampled and digitized X-ray data from the DAS 948 and performs high-speed image reconstruction. The reconstructed images are input to the computer 918 that stores the image in a storage device 952. The computer 918 may also receive commands and scanning parameters from an operator via a console 960 that has a keyboard. An associated visual display unit 962 allows the operator to observe the reconstructed image and other data from computer. It may be noted that one or more of the computer 918, controllers, or the like may be incorporated as part of a processing unit such as the processing unit 120 discussed herein.

The operator supplied commands and parameters are used by the computer 918 to provide control signals and information to the DAS 948, the X-ray controller 944 and the gantry motor controller 946. In addition, the computer 918 operates a table motor controller 964 that controls the motorized table 922 to position the subject 917 in the gantry 910. Particularly, the table 922 moves at least a portion of the subject 917 through the gantry opening.

In various embodiments, the computer 918 includes a device 970, for example, a CD-ROM drive, DVD drive, magnetic optical disk (MOD) device, or any other digital device including a network connecting device such as an Ethernet device for reading instructions and/or data from a tangible non-transitory computer-readable medium 972, that excludes signals, such as a CD-ROM, a DVD or another digital source such as a network or the Internet, as well as yet to be developed digital means. In another embodiment, the computer 918 executes instructions stored in firmware (not shown). The computer 918 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the X-ray source 912 and the detector array 914 are rotated with the gantry 910 within the imaging plane and around the subject 917 to be imaged such that the angle at which an X-ray beam 974 intersects the subject 917 constantly changes. A group of X-ray attenuation measurements, i.e., projection data, from the detector array 914 at one gantry angle is referred to as a "view" or "projection." A "scan" of the subject 917 comprises a set of views made at different gantry angles, or view angles, during one or more revolutions of the X-ray source 912 and the detector array 914. In a CT scan, the projection data is processed to reconstruct an image that corresponds to a three-dimensional volume taken of the subject 917. It may be noted that, in some embodiments, an image may be reconstructed using less than a full revolution of data. For example, with a multi-source system, substantially less than a full rotation may be utilized. Thus, in some embodiments, a scan (or slab) corresponding to a 360 degree view may be obtained using less than a complete revolution.

As discussed above, for the example depicted in FIG. 1, the determination module 124 is configured to receive information from one or more imaging units and/or information from the reconstruction module 122 and/or the input unit 150, and to determine, for example, whether a stop criterion has been satisfied or whether a subsequent scan should be performed. In some embodiments, the determination module 124 determines the type of subsequent scan to be performed. Yet further still, alternatively or additionally, the determination module 124 (and/or other aspect of processing unit 120) may be utilized to determine a color scheme for display of an image, such as blood vessels of an image, that may be used in connection with determining whether a stop criterion has been satisfied and/or determination of a subsequent scan.

For example, in some embodiments, with continued reference to FIG. 1, the CT imaging system 100 includes a CT imaging unit 110 (which in turn includes an X-ray source 112 and CT detector 114), a display unit 140, and a processing unit 120. Additionally or alternatively to the configuration of the processing unit 120 discussed above, the processing unit 120 in various embodiments is configured to acquire at least three phases of CT imaging information via the CT imaging unit 110, determine timing information for imaging intensity of blood vessels represented in the CT imaging information, assign corresponding colors to the blood vessels based on the timing information, reconstruct an image using the CT imaging information from the at least three phases, with the blood vessels depicted in the reconstructed image represented using the corresponding colors based on the determined timing information, and display the image on the display unit 140. It may be noted that in addition to providing timing related information, the displayed image may also provide information or a representation regarding how intense the contrast uptake is in one or more vessels. For example, in various embodiments, vessels that do not have an important or intense flow appear more transparent that vessels having a relatively more important or intense flow. Accordingly, in addition to assigning colors to different flows based on timing information, the processing unit 120 may also assign relative transparency or intensity to provided colors to provide information regarding the intensity of the corresponding flow in one or more vessels.

The at least three phases of CT imaging information are acquired at different times. For example, the at least three phases of CT imaging information may be acquired at different times as a contrast agent moves through blood vessels for at least some of the phases. In some embodiments, for example, CTA may be performed to determine and/or identify a blockage in a blood vessel of the brain. In various embodiments, more than three phases may be acquired. For example, an additional phase of CT imaging information may be acquired as non-contrast CT information, or information acquired before the introduction of a contrast agent. Further, more than three phases may be acquired as contrast agent moves through blood vessels. For example, in some embodiments, nine phases may be acquired as contrast agent moves through blood vessels. Generally, the more phases are acquired, the higher the achievable resolution of the timing information (e.g., a time of maximum intensity for a given portion of a blood vessel), while acquiring fewer phases reduces X-ray dose and computational requirements. The particular number of phases acquired may accordingly be tailored for a given particular application.

Figure 9:
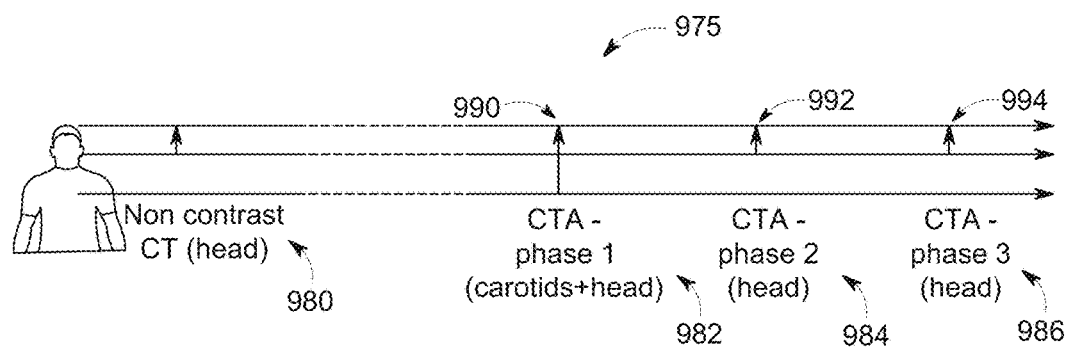
FIG. 9 depicts an example timeline of acquisition of various phases of CT imaging information for a CTA analysis of blood flow in the brain.

FIG. 9 depicts one example timeline 975 of acquisition of various phases of CT imaging information for a CTA analysis of blood flow in the brain. As seen in FIG. 9, the phases acquired for the illustrated example include a pre-contrast phase 980, a first contrast phase 982, a second contrast phase 984, and a third contrast phase 986. The pre-contrast phase 980 is acquired before introduction of contrast agent. CT imaging information acquired at the pre-contrast phase 980 may be understood as pre-contrast information. The pre-contrast information, for example, may be utilized to determine a baseline intensity that may be used (e.g., by the processing unit 120) to determine a relative maximum intensity for information acquired during one or more of the contrast phases.

The contrast phases (first contrast phase 982, second contrast phase 984, and third contrast phase 986) correspond to flow of a contrast agent and are acquired after introduction of a contrast agent. The contrast phases of CT imaging information are acquired at different times. For example, the first contrast phase 982 of CT imaging information may be acquired at a first time 990, the second contrast phase 984 at a second time 992 (in the illustrated embodiment, ten seconds after the first time 990), and the third phase 986 at a third time 994 (in the illustrated embodiment, eighteen seconds after the first time 990). In some embodiments, the phases of CT imaging information acquisition may generally correspond to phases of blood flow through the brain. For example, the first contrast phase 982 of CT imaging information may correspond to an arterial phase of blood flow (e.g., a phase of blood flow during which arteries experiencing normal flow reach an imaging intensity peak), the second contrast phase 984 of CT imaging information may correspond to a venous phase of blood flow (e.g., a phase of blood flow during which veins experiencing normal flow reach an imaging intensity peak), and the third contrast phase 986 of CT imaging information may correspond to a post-venous phase of blood flow (e.g., a phase of blood flow during which arteries experiencing delayed flow reach an imaging intensity peak). However, it may be noted that in other embodiments the phases of CT imaging information acquisition need not directly correspond to particular phases of blood flow.

Figure 10:
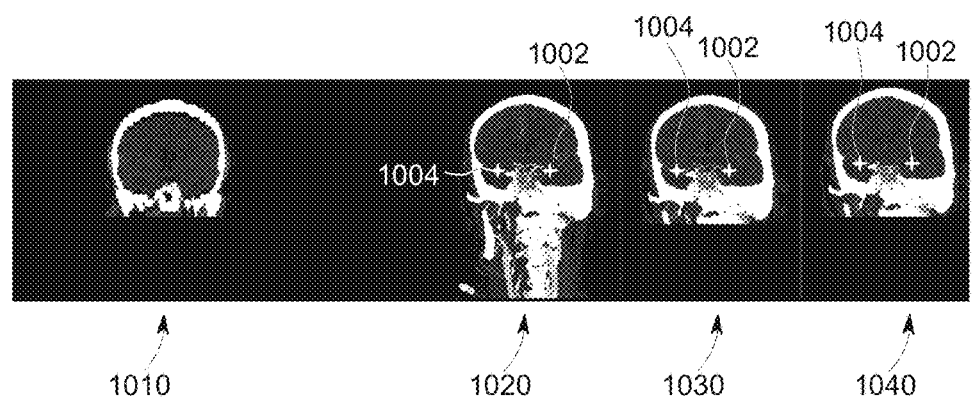
FIG. 10 depicts example images corresponding to the phases of CT imaging information acquisition of FIG. 9.

FIG. 10 depicts example images corresponding to the phases of CT imaging information acquisition of FIG. 9. FIG. 10 includes a pre-contrast image 1010 (acquired during pre-contrast phase 910), a first contrast phase image 1020 (acquired during first contrast phase 920), a second contrast phase image 1030 (acquired during second contrast phase 930), and a third contrast phase image 1040 (acquired during third contrast phase 940). For the example discussed in connection with FIG. 10, imaging of two vessels (a normal artery 1002 on the right side of the brain as seen in FIG. 10, and a delayed artery 1004 on the left side of the brain as in FIG. 10) will be discussed. The normal artery 1002 may be understood as having normal or unblocked flow, while the delayed artery 1004 experiences delayed flow (e.g., delayed due to a blockage in the delayed artery 1004 that does not completely block flow).

After introduction of a contrast agent, information from the first contrast phase 920 of acquisition is used to reconstruct first contrast phase image 1020. Similarly, information from the second contrast phase 930 of acquisition is used to reconstruct second contrast phase image 1030, and information from the third contrast phase 940 of acquisition is used to reconstruct third contrast phase image 1040. Intensities for both the normal artery 1002 and delayed artery 1004 are then determined for each image.

Figure 11:
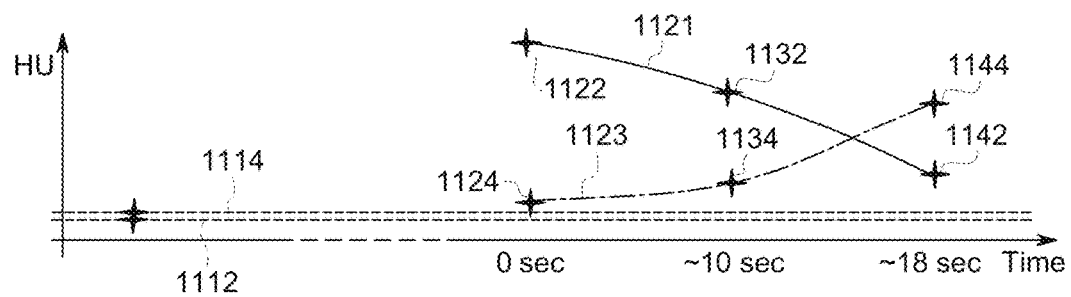
FIG. 11 depicts example intensities for the various images of FIG. 10.

FIG. 11 depicts example intensities for the various images of FIG. 10 including normal intensity curve 1121 for the normal artery 1002 and delayed intensity curve 1123 for the delayed artery 1004. As seen in FIG. 11, the intensity of the pre-contrast image 1010 at a location corresponding to the normal artery 1002 provides baseline 1112. Also, the intensity of the pre-contrast image 1010 at a location corresponding to the delayed artery 1004 provides baseline 1114.

Further, the intensity of the first contrast image 1020 at the normal artery 1002 provides point 1122 of normal intensity curve 1121 for the normal artery 1002, and the intensity of the first contrast image 1020 at the delayed artery 1004 provides point 1124 of delayed intensity curve 1123 for the delayed artery 1004. Also, the intensity of the second contrast image 1030 at the normal artery 1002 provides point 1132 of normal intensity curve 1121, and the intensity of the second contrast image 1030 at the delayed artery 1004 provides point 1134 of delayed intensity curve 1123. Similarly, the intensity of the third contrast image 1040 at the normal artery 1002 provides point 1142 of normal intensity curve 1121, and the intensity of the third contrast image 1040 at the delayed artery 1004 provides point 1144 of delayed intensity curve 1123. Generally, an intensity for each voxel of an imaging volume of interest may be plotted for each acquired phase to generate a curve for each voxel of intensity over time. Then, the timing information may be determined individually for each voxel to determine the coloring for that particular voxel in a reconstructed image using imaging information from the acquired phases. For example, the timing information may be based on a maximum intensity of the CT imaging information over time on a voxel-by-voxel bases. Accordingly, in various embodiments, a time describing or corresponding to a point of maximum intensity for that particular voxel may be used to determine which color will be used to depict the voxel in an image.

In the example illustrated in FIG. 11, the normal intensity curve 1121 has a peak value at 1122 (or t=0 seconds), and the delayed intensity curve 1123 has a peak value at 1144 (or t=18 seconds). Accordingly, the voxel(s) associated with the normal artery 1102 may be assigned a first color associated with t=0 seconds (or associated with range of time including t=0 seconds), while the voxel(s) associated with the delayed artery 1104 may be assigned a different color associated with t=18 seconds (or associated with a range of time including t=18 seconds).

For example, in some embodiments, a first color of a reconstructed image using information from the CT imaging acquisition phases corresponds to an arterial phase (e.g., voxels of blood vessels having a maximum intensity within a range of time corresponding to an arterial phase are assigned the first color). Also, a second color of the reconstructed image corresponds to a venous phase (e.g., voxels of blood vessels having a maximum intensity within a range of time corresponding to a venous phase are assigned the second color). Further, a third color of the reconstructed image corresponds to a post-venous or delayed phase (e.g., voxels of blood vessels having a maximum intensity within a range of time corresponding to a post-venous or delayed phase are assigned the third color). For example, in some embodiments, the first color is red, the second color is green, and the third color is blue. Accordingly, blood vessels that reach a maximum intensity (e.g., due to the present of contrast agent) during the arterial phase of blood flow are depicted in red, blood vessels that reach a maximum intensity during the venous phase of blood flow are depicted in green, and blood vessels that reach a maximum intensity during the post-venous or delayed phase of blood flow are depicted in blue. With the time periods set appropriately, the vessels appearing as red in the image may be understood as having normal flow and the vessels appearing in blow may be understood as having delayed flow, thereby helping to determine where a blockage occurs and the extent of damage to the brain due to the blockage.

Figure 12:
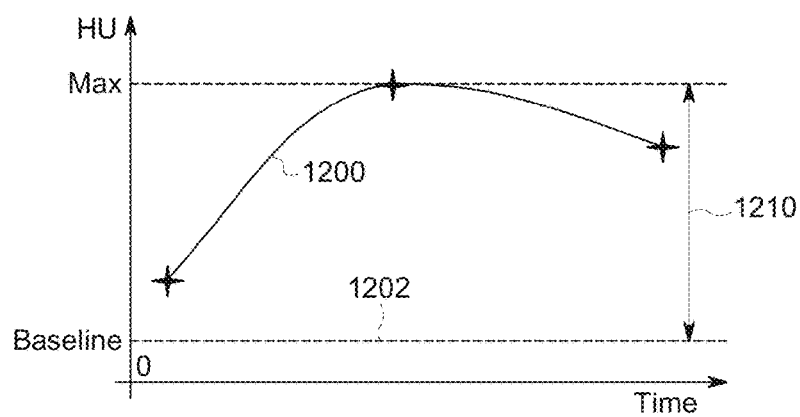
FIG. 12 depicts an example plot that includes an intensity curve and a baseline for a particular voxel in accordance with various embodiments.

FIG. 12 depicts an example plot that includes an intensity curve 1200 and a baseline 1202 for a particular voxel. Intensity values for the intensity curve 1200 are obtained at different times after the introduction of a contrast agent, and the intensity for the baseline 1202 is obtained before introduction of the contrast agent. The example intensity curve 1200 depicted in FIG. 12 experiences a maximum at an intermediate time corresponding to a venous phase of blood flow and may be understood as describing a voxel of a vein. As seen in FIG. 12, the intensity curve 1200 is a plot of intensity (e.g., in Houndsfield units) over time. A relative enhancement 1210 may be measured as the difference between the intensity curve 1200 and the baseline 1202, and represents the enhancement of the voxel at a given time due to the contrast agent. The plot of FIG. 12 may be used to generate a maximum intensity image, which shows the intensity of vessels over time. Such an image provides a summary of intensity of plural images acquired at different times. The image may be generated for each voxel as a temporal maximum of the CTA value. The plot of FIG. 12 may also be used to generate a relative enhancement image that depicts the difference between the measured intensities at different times with contrast relative to a baseline intensity obtained for corresponding voxels without contrast (e.g., acquired before the contrast agent was introduced). It may be noted that a view for a slice of a volume generated using such a maximum intensity image or relative enhancement image may be combined with other slices to show vessels above and below a current slice location. Relative enhancement may be used in various embodiments to reduce the effects of noise and/or to account for imaging intensity caused by background structures or tissue.

Figure 13:
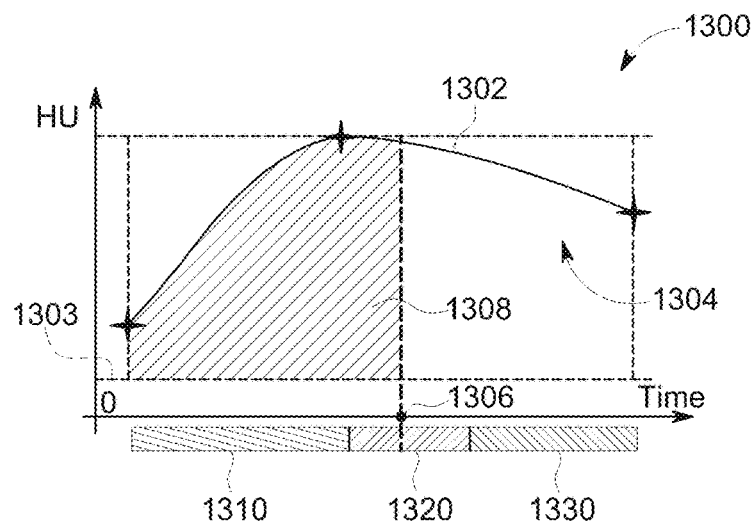
FIG. 13 depicts an example plot of intensity over time for a particular voxel in accordance with various embodiments.

In various embodiments, the processing unit 120 is configured to, for individual voxels of the CT imaging information, generate a plot of intensity over time, determine an area under a curve defined by the plot and determine the timing information (which will be used to assign a color to the particular voxel) using the area under the curve. FIG. 13 depicts an example plot 1300 of intensity over time for a particular voxel. The plot 1300 includes a curve 1302 defined by the intensity over time, including a baseline 1303 corresponding to an intensity value in the absence of contrast agent. For example, three or more phases of imaging information may be acquired and a point for the intensity of each phase plotted against the time for the corresponding phase, with the curve 1302 fit to the plotted points. An area 1304 is defined under the curve 1302, and is used in various embodiments to determine the timing information. The area 1304 under the curve 1302 correlates to blood volume, and may be used to determine the timing information (e.g., based on a time at which a predetermined fraction of the blood volume or area 1304 has been achieved). For example, the timing information may be determined for a particular voxel based on a time required to achieve half of the total area under the corresponding curve generated for the particular voxel.

In the illustrated embodiment, a time 1306 is shown that corresponds to the achievement of half of the total area 1304 (shown as shaded area 1308). Three time ranges are shown—a first time range 1310 (e.g., a red time range for arterial flow), a second time range 1320 (e.g., a green time range for venous flow), and a third time range 1330 (e.g., a blue time range for delayed arterial flow). For the example curve 1302, half of the area 1304 under the curve 1302 is achieved at time 1306 which occurs during the second time range 1320. Accordingly, the voxel corresponding to the curve 1302 would be colored with a color associated with the second time range 1320 (e.g., green). A similar process is performed for each voxel of an imaging volume of interest and used to generate a combined image. Accordingly, a series of intermediate images corresponding to acquisition phases may be used to determine intensities over time that are plotted to determine timing information corresponding to blood flow, which is in turn used to colorize a final or combined image that uses different colors to indicate the timing of blood flow through vessels.

Figure 14:
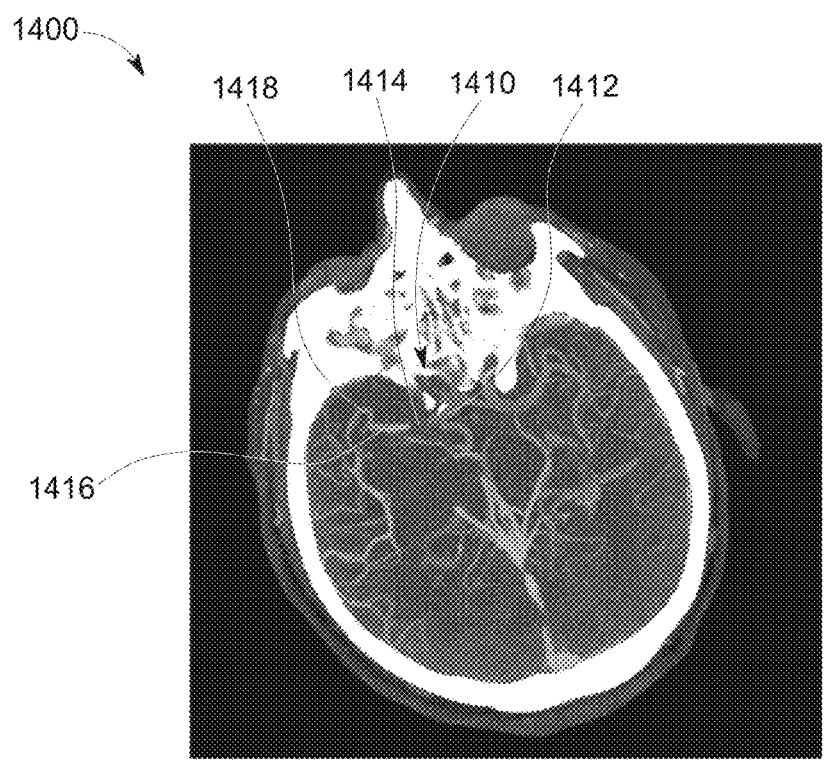
FIG. 14 depicts an axial view of a head that is generated using determined timing information in accordance with various embodiments.

FIG. 14 depicts an axial view 1400 of a head that is generated using timing information determined using plots similar to those described in connection with FIG. 13. As seen in FIG. 14, a vessel 1410 includes a first portion 1412 that is a first color corresponding to flow during an arterial phase (e.g., red), a second portion 1414 that is not colorized (e.g., black), a third portion 1416 that is a second color corresponding to flow during a venous phase (e.g., green), and a fourth portion 1418 that is a third color corresponding to flow during a post-venous or delay phase (e.g., blue). The view 1400 may be used to determine the location and effect of a blockage. For example, in the illustrated portion, the first portion 1412 is colorized (e.g., red) to indicate normal arterial flow. However, the second portion 1414 is not colorized, showing little or no enhancement due to the contrast agent, and may be identified as representing a blockage. Downstream of the blockage or second portion 1414, the third portion 1416 (e.g., green for venous phase of flow) and fourth portion 1418 (e.g., blue for delayed phase of flow) indicate flow that is progressively later than the arterial phase. Thus, blood flow may be understood as reaching the portion of the brain near the third portion 1416 and fourth portion 1418, so that the corresponding portion of the brain is not dead, but is receiving delayed flow. Accordingly, the view 1400 may be employed to determine the location of a blockage (e.g, second portion 1414) as well as the extent of damage being done by the blockage. For example, if the third portion 1416 and fourth portion 1418 were not colored, but instead uncolored (e.g., black) indicating no contrast enhancement or no blood flow, the corresponding portion of the brain may be understood as being dead. It may be noted that other views (e.g., coronal, sagittal) may be generated alternatively or additionally.

Figure 15:
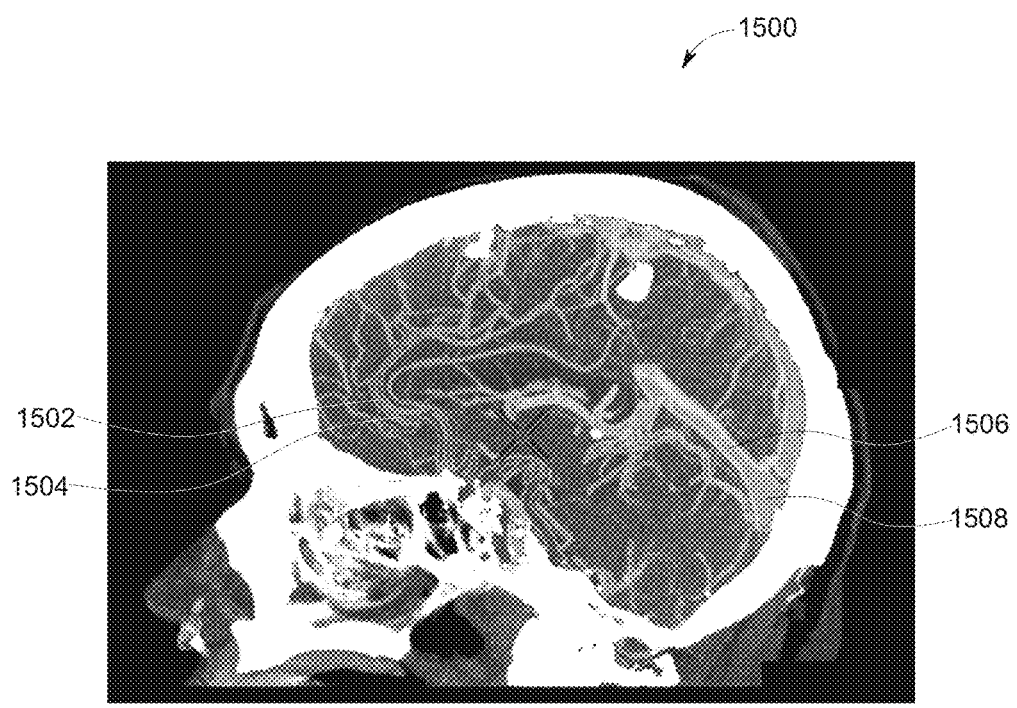
FIG. 15 depicts an example side view of a brain with colorized vessels in accordance with various embodiments.

In various embodiments, the processing unit 120 autonomously assigned the corresponding colors based on ranges of time. For example, the processing unit 120 may use predetermined, default ranges of time to set the color (e.g., a time of maximum intensity and/or a time corresponding to an area under a curve). To provide for adjustability of timing (e.g., for instances where timing of blood flow varies from a predetermined value, such as for a blood flow rate that is faster or slower than expected), in some embodiments, the processing unit 120 adjusts the ranges of time responsive to a user input (e.g., provided via input unit 150). For example, FIG. 15 depicts an example side view 1500 of a brain with colorized vessels. The view 1500 includes a vessel 1502 positioned proximate the front of the brain having a first color 1504 (e.g., red for normal arterial flow). The view 1500 includes a vessel 1506 positioned proximate the back of the brain having a second color 1508 (e.g., green for venous flow). Flow toward the back of the brain would be expected to be in the venous phase of blood flow, and, accordingly, a user viewing the view 1500 and observing the green color for venous flow for vessel 1506 may conclude that the color scheme is appropriate. However, if the vessel 1506 toward the back of the brain exhibited a different color, the user may determine that the colorization scheme is not appropriate and adjust the time ranges. The processing unit 120 may refresh the view after each adjustment, with subsequent adjustments performed until an expected or desired colorization for vessels toward the back of the brain is achieved.

It may be noted that additional processing of imaging information may be performed before (and/or after) generating intensity profiles over time and determine timing information. For example, the processing unit 120 may perform motion correction before determine the timing information. Motion correction may be used to help insure accurate registration between corresponding voxels of image acquisition phases acquired at different times. As another example, bone removal may be performed to improve visualization of vessels.

Figure 16:
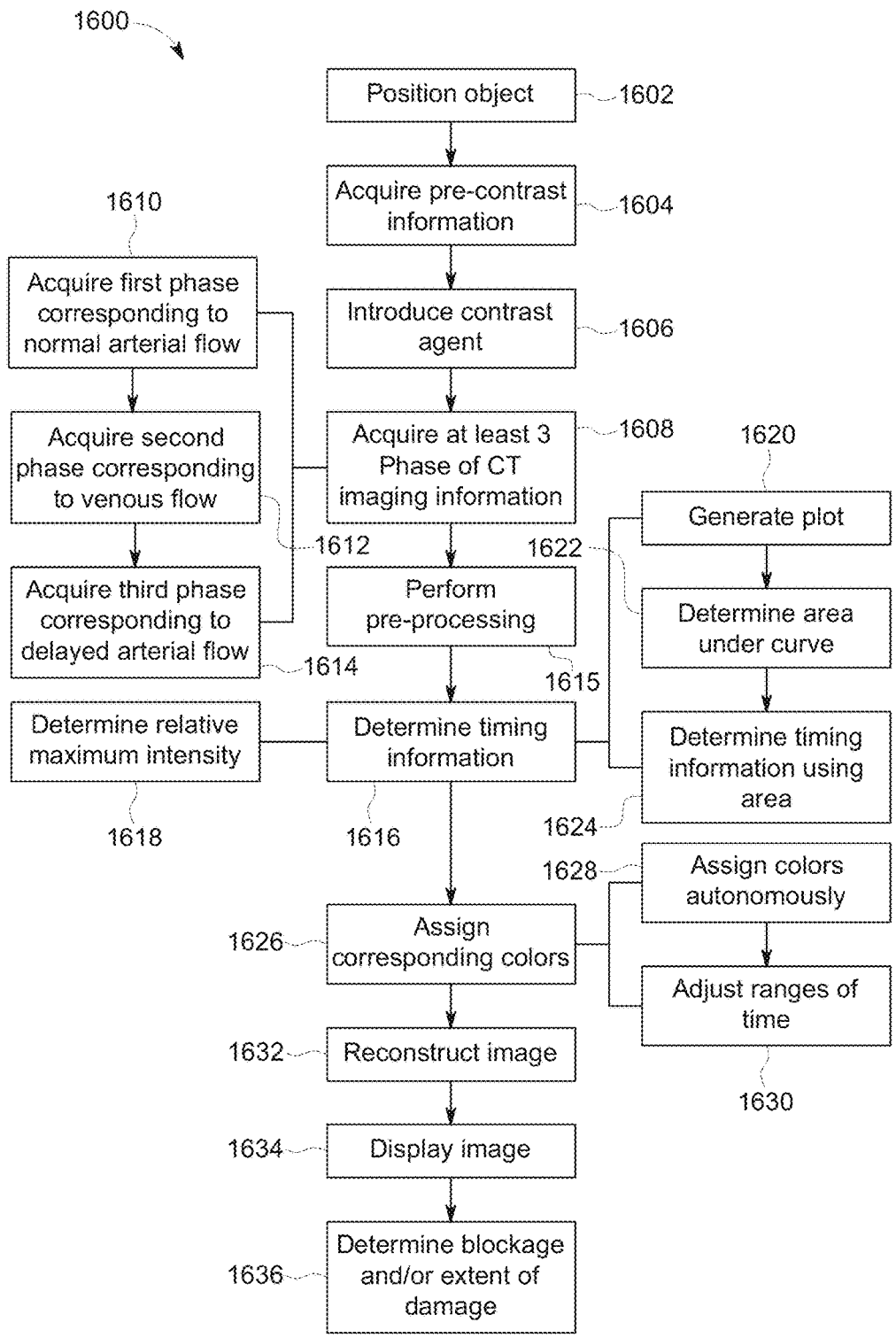
FIG. 16 is a flowchart of a method in accordance with various embodiments.

FIG. 16 provides a flowchart of a method 1600 for determining and depicting blood flow, for example for a patient as part of a stroke analysis, in accordance with various embodiments. The method 1600, for example, may employ or be performed by structures or aspects of various embodiments (e.g., systems and/or methods) discussed herein (e.g., as part of or in connection with steps 222-230 of method 200). In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 1600 may be able to be used as one or more algorithms to direct hardware (e.g., one or more aspects of the processing unit 120) to perform one or more operations described herein.

At 1602, an object to be imaged (e.g., patient is positioned). For example, the object may be a human patient positioned on a table in a bore of a CT acquisition unit (e.g., CT acquisition unit 110). The head of the patient in various embodiments is positioned in the bore to perform imaging to determine blood flow in the brain for determination of blockage location and/or extent of damage caused by a blockage.

At 1604, pre-contrast information is acquired. The pre-contrast information is acquired (e.g., using the CT acquisition unit 110) before any contrast agent is introduced into the patient being imaged. The pre-contrast information may be used for example, to provide a baseline intensity for each voxel to be used in determining a relative amount of contrast enhancement attributable to contrast agent for subsequent images. Use of such pre-contrast information and a baseline helps reduce the effects of noise and/or background structures.

At 1606, contrast agent is introduced into the object to be imaged (patient). The amount, timing, and type of contrast agent is selected so that the contrast agent will pass through the vessels of the patient's brain for use in determining and depicting blood flow through the brain.

At 1608, at least three phases of CT imaging information is acquired (e.g., using the CT acquisition unit 110). The at least three phases of CT imaging information acquired at 1608 are acquired as contrast agent flows through the vessels of the brain to provide contrast enhancement. The phases are acquired at different times to determine corresponding intensities attributable to the contrast agent.

In the illustrated embodiment, at 1610, a first phase of imaging information corresponding to normal arterial flow is acquired (e.g., at a first time). At 1612, a second phase of imaging information corresponding to venous flow is acquired (e.g., at a second time after the first time, for instance 10 seconds after the first time). At 1614, a third phase of imaging information corresponding to post-venous or delayed arterial flow is acquired (e.g., at a third time after the second time, for instance 18 seconds after the first time). It may be noted that additional phases may be acquired in various embodiments. It may further be noted that the acquisition phases need not have a 1:1 or direct correspondence to blood flow phases (e.g., arterial, venous, post-venous).

At 1615, pre-processing is performed on the acquired CT imaging information. For example, motion correction may be performed. As another example, bone removal (e.g., using a bone mask) may be performed.

At 1616, timing information is determined (e.g., using processing unit 120). The timing information corresponds to imaging intensity of blood vessels represented in the CT imaging information. The level or variation of intensity of the voxels of the various images over time corresponds to the amount of enhancement due to contrast agent passing through the vessels. The timing information may be used to determine a color scheme used to distinguish vessels based on the time of flow of contrast agent through the vessels. In various embodiments, the timing information is determined using a plot or representation of intensity (e.g., relative enhancement due to contrast agent) over time. It may be noted that, as used herein, a plot need not be printed or displayed, but instead may refer to a determined relationship between intensity and time. The plots and/or timing information in various embodiments are determined separately for each individual voxel, or on a voxel-by-voxel basis. At 1618, a relative maximum intensity is determined using the baseline from the pre-contrast information for each voxel being analyzed. The relative maximum intensity may represent a maximum measured value, or may represent a maximum point on a curve fitted to measured points. Alternatively or additionally, the timing information may be determined using an area under a curve of intensity over time (e.g., based on achievement of a predetermined fraction or proportion of the total area under the curve).

For example, as seen in FIG. 16, at 1620, a plot of intensity over time is generated for individual voxels of the CT imaging information (e.g., voxels corresponding to blood vessels; voxels surpassing a threshold level of contrast enhancement). A curve may be fit to the intensities determined for each of the acquired phases for the particular voxel. At 1622, an area under the curve defined by the plot of intensity over time is determined. The area under the curve corresponds to the volume of blood flow. At 1624, the timing information is determined using the area under the curve. For example, a time may be determined at which half of the total area under the curve (or other pre-determined proportion or fraction) is achieved, with the determined time used to determine the colorization for the particular voxel being analyzed.

At 1626, corresponding colors are assigned to blood vessels based on the timing information. The colors may be assigned on a voxel-by-voxel basis. For example, in some embodiments, voxels having a peak intensity (or achievement of a predetermined fraction of total area under an intensity curve) occurring over a first range of time are assigned a first color, voxels having a peak intensity (or achievement of a predetermined fraction of total area under an intensity curve) occurring over a second range of time are assigned a second color, and voxels having a peak intensity (or achievement of a predetermined fraction of total area under an intensity curve) occurring over a third range of time are assigned a third color. For instance, in some embodiments, voxels having timing information corresponding to normal arterial flow are colored red, voxels having timing information corresponding to venous flow are colored green, and voxels having timing information corresponding to delayed arterial flow (e.g., delayed due to a blockage) are colored blue.

At 1628 of the illustrated embodiment, the colors are assigned autonomously (e.g., by processing unit 120) based on ranges of time. At 1630, the ranges of time used to assign the color are adjustment responsive to a user input (e.g., as discussed above).

At 1632, an image is reconstructed. In the illustrated embodiment, the image is reconstructed using CT imaging information from all of the phases of acquisition. The blood vessels in the reconstructed image are depicted being colorized based on the timing information. Accordingly, the reconstructed may be used to quickly, conveniently, and accurately determine which vessels are generally experiencing flow at which times or phases of blood flow At 1634, the image is displayed (e.g., using display unit 140). The displayed image may be used, for example, to provide any adjustments to the timing/colorization scheme. The displayed image may also be used for diagnostic purposes.

At 1636, a blockage and/or amount of damage is determined. For example, a point of transition in a blood vessel away from normal arterial flow and toward delayed arterial flow may be determined based on a change or changes in the color of voxels of the blood vessel, and used to locate a blockage. The blockage may itself be represented by an uncolored portion, and may have a portion of the blood vessel colored as having venous flow located next to it. If there is delayed flow downstream of the blockage, it may be determined that the associated portion of the brain is still live and receiving blood (albeit delayed due to a blockage); however, if the portion downstream of the blockage does not have colorization corresponding to venous and/or delayed arterial flow, it may be determined that the corresponding portion of the brain is not receiving blood and is dead.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A computed tomography (CT) imaging system comprising:
    a CT imaging unit comprising an X-ray source and a CT detector;
    a display unit; and
    at least one processor operably coupled to the imaging unit and the display unit, the at least one processor configured to:
        acquire at least three phases of CT imaging information via the CT imaging unit;
        determine timing information for imaging intensity of blood vessels represented in the CT imaging information;
        assign corresponding colors to the blood vessels based on the timing information;
        reconstruct an image using the CT imaging information from the at least three phases, wherein the blood vessels depicted in the reconstructed image are represented using the corresponding colors based on the timing information; and
        display the image on the display unit.

2. The CT imaging system of claim 1, wherein the at least one processor is configured to determine the timing information based on a maximum intensity of the CT imaging information over time on a voxel-by-voxel basis.

3. The CT imaging system of claim 1, wherein the corresponding colors include a first color corresponding to a an arterial phase of blood flow, a second color corresponding to a venous phase of blood flow, and a third color corresponding to a third phase corresponding to a post-venous phase of blood flow.

4. The CT imaging system of claim 1, wherein the at least three phases comprise phases corresponding to flow of a contrast agent, and wherein the CT imaging information includes pre-contrast information acquired before introduction of the contrast agent, wherein the at least one processor is further configured to determine a relative maximum intensity using a baseline from the pre-contrast information.

5. The CT imaging system of claim 1, wherein the at least one processor is configured to, for individual voxels of the CT imaging information, generate a plot of intensity over time, determine an area under a curve defined by the plot, and determine the timing information using the area under the curve.

6. The CT imaging system of claim 5, wherein the timing information is determined for the individual voxels based on a time corresponding to achieving half of the corresponding area under the curve.

7. The CT imaging system of claim 1, wherein the at least one processor is configured to autonomously assign the corresponding colors based on ranges of time.

8. The CT imaging system of claim 7, wherein the at least one processor is configured to adjust the ranges of time responsive to a user input.

9. The CT imaging system of claim 1, wherein the at least one processor is configured to motion correct the CT imaging information from the at least three phases before determining the timing information.

10. A method comprising:
    acquiring at least three phases of computed tomography (CT) imaging information via a CT imaging unit that comprises an X-ray source and a CT detector;

determining, using at least one processor, timing information for imaging intensity of blood vessels represented in the CT imaging information;

assigning corresponding colors to the blood vessels based on the timing information;

reconstructing an image using the CT imaging information from the at least three phases, wherein the blood vessels depicted in the reconstructed image are represented using the corresponding colors based on the timing information; and displaying the image on a display unit.

11. The method of claim 10, wherein the timing information is determined based on a maximum intensity of the CT imaging information over time on a voxel-by-voxel basis.

12. The method of claim 10, wherein acquiring the at least three phases comprises acquiring a first phase corresponding to an arterial phase of blood flow, a second phase corresponding to a venous phase of blood flow, and a third phase corresponding to a post-venous phase of blood flow, and wherein the corresponding colors include a first color corresponding to the arterial phase of blood flow, a second color corresponding to the venous phase of blood flow, and a third color corresponding to the post-venous phase of blood flow.

13. The method of claim 10, further comprising:
acquiring pre-contrast information;
after acquiring the pre-contrast information, introducing a contrast agent into an object to be imaged, wherein the at least three phases comprise phases corresponding to flow of the contrast agent through the object; and
determining a relative maximum intensity using a baseline from the pre-contrast information.

14. The method of claim 10, further comprising:
generating, for individual voxels of the CT imaging information, a plot of intensity over time;
determining an area under a curve defined by the plot; and
determining the timing information using the area under the curve.

15. The method of claim 14, wherein the timing information is determined for each voxel based on a time corresponding to achieving half of the corresponding area under the curve.

16. The method of claim 10, further comprising autonomously assigning the corresponding colors based on ranges of time.

17. The method of claim 16, further comprising adjusting the ranges of time responsive to a user input.

18. The method of claim 10, further comprising motion correcting the CT imaging information from the at least three phases before determining the timing information.

19. A tangible and non-transitory computer readable medium comprising one or more computer software modules configured to direct one or more processors to:
acquire at least three phases of computed tomography (CT) imaging information via a CT imaging unit that comprises an X-ray source and a CT detector;
determine timing information for imaging intensity of blood vessels represented in the CT imaging information;
assign corresponding colors to the blood vessels based on the timing information;
reconstruct an image using the CT imaging information from the at least three phases, wherein the blood vessels depicted in the reconstructed image are represented using the corresponding colors based on the timing information; and
display the image on a display unit.

20. The tangible and non-transitory computer readable medium of claim 19, wherein the computer readable medium is further configured to:
generate, for individual voxels of the CT imaging information, a plot of intensity over time;
determine an area under a curve defined by the plot; and
determine the timing information using the area under the curve.

21. The CT imaging system of claim 1, wherein the at least one processor is configured to at least one of determine or identify a blockage in at least one of the blood vessels using the image.

22. The method of claim 10, further comprising at least one of determining or identifying a blockage in at least one of the blood vessels using the image.

23. The tangible and non-transitory computer readable medium of claim 19, wherein the computer readable medium is further configured to at least one of determine or identify a blockage in at least one of the blood vessels using the image.

* * * * *